United States Patent
Gruner et al.

(10) Patent No.: US 9,084,732 B2
(45) Date of Patent: *Jul. 21, 2015

(54) COSMETIC FORMULATIONS COMPRISING HIGH GLOSS NON-METALLIC SILVER-COLORED PIGMENTS

(75) Inventors: Michael Gruner, Auerbach (DE); Thomas Schneider, Lauf a. d. Pegnitz (DE); Gunter Kaupp, Neuhaus (DE); Christian Rummer, Nuremberg (DE); Dirk Schumacher, Pegnitz (DE)

(73) Assignee: Eckart GmbH, Hartenstein (DE)

( * ) Notice: Subject to any disclaimer, the term of this patent is extended or adjusted under 35 U.S.C. 154(b) by 193 days.

This patent is subject to a terminal disclaimer.

(21) Appl. No.: 13/428,567

(22) Filed: Mar. 23, 2012

(65) Prior Publication Data

US 2012/0301521 A1    Nov. 29, 2012

(30) Foreign Application Priority Data

Mar. 25, 2011    (DE) .......................... 10 2011 001 579

(51) Int. Cl.
*A61K 8/19* (2006.01)
*A61K 8/29* (2006.01)
*A61Q 1/06* (2006.01)
*A61Q 1/10* (2006.01)
*A61Q 5/06* (2006.01)
(Continued)

(52) U.S. Cl.
CPC ................ *A61K 8/29* (2013.01); *A61K 8/0254* (2013.01); *A61K 8/19* (2013.01); *A61Q 1/04* (2013.01); *A61Q 1/06* (2013.01); *A61Q 1/10* (2013.01); *A61Q 1/12* (2013.01); *A61Q 3/02* (2013.01); *A61Q 5/06* (2013.01); *A61Q 19/00* (2013.01); *A61Q 19/10* (2013.01); *C01B 31/0423* (2013.01); *C09C 1/0015* (2013.01); *C09C 1/0021* (2013.01); *A61K 2800/436* (2013.01); *C01P 2004/51* (2013.01); *C01P 2006/62* (2013.01); *C01P 2006/63* (2013.01); *C01P 2006/64* (2013.01); *C01P 2006/65* (2013.01); *C01P 2006/66* (2013.01); *C01P 2006/80* (2013.01); *C09C 2200/102* (2013.01); *C09C 2200/202* (2013.01); *C09C 2200/301* (2013.01)

(58) Field of Classification Search
USPC ......................................................... 424/401
See application file for complete search history.

(56) References Cited

U.S. PATENT DOCUMENTS

| 4,867,793 | A | 9/1989 | Franz et al. |
| 5,972,098 | A | 10/1999 | Andes et al. |

(Continued)

FOREIGN PATENT DOCUMENTS

| DE | 10331903 A1 | 2/2004 |
| DE | 10320455 A1 | 11/2004 |

(Continued)

OTHER PUBLICATIONS

BYK-GARDNER, KATALOG "Qualitatskontrolle fur Lacke and Kunstoffe" 2011/2012, S. 97/98.

(Continued)

*Primary Examiner* — Michael B Pallay
(74) *Attorney, Agent, or Firm* — The Webb Law Firm

(57) ABSTRACT

The present invention relates to a cosmetic formulation including a cosmetically acceptable medium and at least one silver-colored pigment, the silver-colored pigment including a nonmetallic platelet-shaped substrate and at least one ilmenite-containing coating.

7 Claims, 2 Drawing Sheets

(51) Int. Cl.
*A61Q 19/00* (2006.01)
*A61Q 19/10* (2006.01)
*C09C 1/00* (2006.01)
*A61Q 1/04* (2006.01)
*A61Q 1/12* (2006.01)
*A61K 8/02* (2006.01)
*C01B 31/04* (2006.01)
*A61Q 3/02* (2006.01)

(56) References Cited

U.S. PATENT DOCUMENTS

| | | | |
|---|---|---|---|
| 7,413,599 | B2 | 8/2008 | Henglein et al. |
| 7,611,574 | B2 | 11/2009 | Kniess et al. |
| 2007/0028799 | A1* | 2/2007 | Kniess et al. ............. 106/31.6 |
| 2007/0243149 | A1 | 10/2007 | Hofacker et al. |
| 2011/0226161 | A1 | 9/2011 | Schumacher et al. |
| 2011/0251303 | A1 | 10/2011 | Rathschlag et al. |
| 2012/0219607 | A1 | 8/2012 | Schmidt et al. |

FOREIGN PATENT DOCUMENTS

| | | | |
|---|---|---|---|
| DE | 102008064202 | A1 | 6/2010 |
| DE | 102009037935 | A1 | 2/2011 |
| DE | 102009049413 | A1 | 4/2011 |
| EP | 0246523 | A2 | 11/1987 |
| EP | 0289240 | A1 | 11/1988 |
| EP | 0681009 | B1 | 9/1998 |
| EP | 0723997 | B1 | 6/1999 |
| EP | 1682622 | B1 | 8/2007 |
| EP | 1980594 | B1 | 6/2009 |
| WO | 9743348 | A1 | 11/1997 |
| WO | 2004056716 | A1 | 7/2004 |
| WO | 2004099319 | A2 | 11/2004 |
| WO | 2005063637 | A1 | 7/2005 |
| WO | 2007115675 | A2 | 10/2007 |

OTHER PUBLICATIONS

Nancy M. Hepp et al., "Determination of total lead in lipstick: Development and validation of a microwave-assisted digestion, inductively coupled plasma-mass spectrometric method" J. Cosmet. Sci., Jul./Aug. 2009, pp. 405-414, vol. 60.

Roman Maisch, "New effect pigments from grey to black" Progress in Organic Coatings, 1993, pp. 261-272, vol. 22.

Schellenberger et al., "Schmelzvorgang unter der Lupe", Farbe & Lack, Apr. 2007, p. 130 (10 pages including partial English translation).

* cited by examiner

COSMETIC FORMULATIONS COMPRISING HIGH GLOSS NON-METALLIC SILVER-COLORED PIGMENTS

BACKGROUND OF THE INVENTION

1. Field of the Invention

The present invention relates to a cosmetic formulation comprising a cosmetically acceptable medium and at least one silver-colored pigment, the silver-colored pigment comprising a nonmetallic platelet-shaped substrate and at least one ilmenite-containing coating.

2. Description of Related Art

The use of silver-colored effect pigments in cosmetic formulations is subject to strict regulatory impositions with regard to the size and nature of the pigment employed. For example, according to FDA Code of Federal Regulation Title 21, Volume 1, 73.1645 in the USA, aluminum effect pigments which do not pass fully through a screen with a mesh size of 200 mesh may not be used in the color cosmetics sector. According to this ordinance, furthermore, the use of aluminum effect pigments is not permitted in the area of the lips and of the mouth in cosmetic formulations. Consequently, for example, global marketing approaches for lipsticks which contain aluminum effect pigments are not possible. From the standpoint of market strategy, such restriction is undesirable.

If it is desired to have the metallic effect and the visual impression of an aluminum effect pigment in a cosmetic formulation, then it is not possible simply to replace the aluminum effect pigment by a silver-colored pearlescent pigment. In terms of their optical properties, metallic effect pigments and pearlescent pigments differ fundamentally from one another.

Metallic effect pigments have a hard metallic specular gloss, whereas pearlescent pigments exhibit a soft velvety gloss which appears to come from deep down.

Commercial silver-colored pearlescent pigments generally do not possess the neutral silver hue that is characteristic of aluminum effect pigments. Nor can the opacity of opaque metallic effect pigments be achieved by pearlescent pigments, which are typically transparent. There is a need, therefore, for pigments for cosmetic formulations that in terms of the optical properties such as, for example, silver color with metallic appearance, opacity, metallic gloss or light/dark flop, come close to metallic effect pigments, and yet contain no metal, such as aluminum, for example. Furthermore, in addition to the criteria already specified, the intention is to provide heavy-metal-free and more light-stable alternatives to silver-colored pigments consisting of or comprising bismuth oxychloride.

The problem on which the present invention was based was that of providing a cosmetic formulation which comprises water-stable, high-gloss, silver-colored pigments. In terms of their visual impression, the silver-colored pigments are to have the properties characteristic of metallic effect pigments. In terms of their appearance, the silver-colored pigments are to differ not at all, or only insubstantially, from commercial aluminum effect pigments. At the same time, the silver-colored pigments are to be distinguished by a high stability, especially with respect to acids, bases, acidic or alkaline cosmetic ingredients, and aqueous or protically/aprotically polar media, and also by their temperature stability. Furthermore, the silver-colored pigments, which are to be suitable for use in the cosmetic formulation, are to be free-flowing and have no propensity toward dust explosion.

SUMMARY OF THE INVENTION

The problem on which the invention is based has been solved through the provision of a cosmetic formulation which comprises a cosmetically acceptable medium and at least one silver-colored pigment, the silver-colored pigment comprising a nonmetallic platelet-shaped substrate and at least one ilmenite-containing coating.

Preferred developments of the cosmetic formulation of the invention are specified in the dependent claims.

BRIEF DESCRIPTION OF THE DRAWINGS

The foregoing summary, as well as the following detailed description, will be better understood when read in conjunction with the appended drawings. In the drawings.

DETAILED DESCRIPTION

Figure 1:
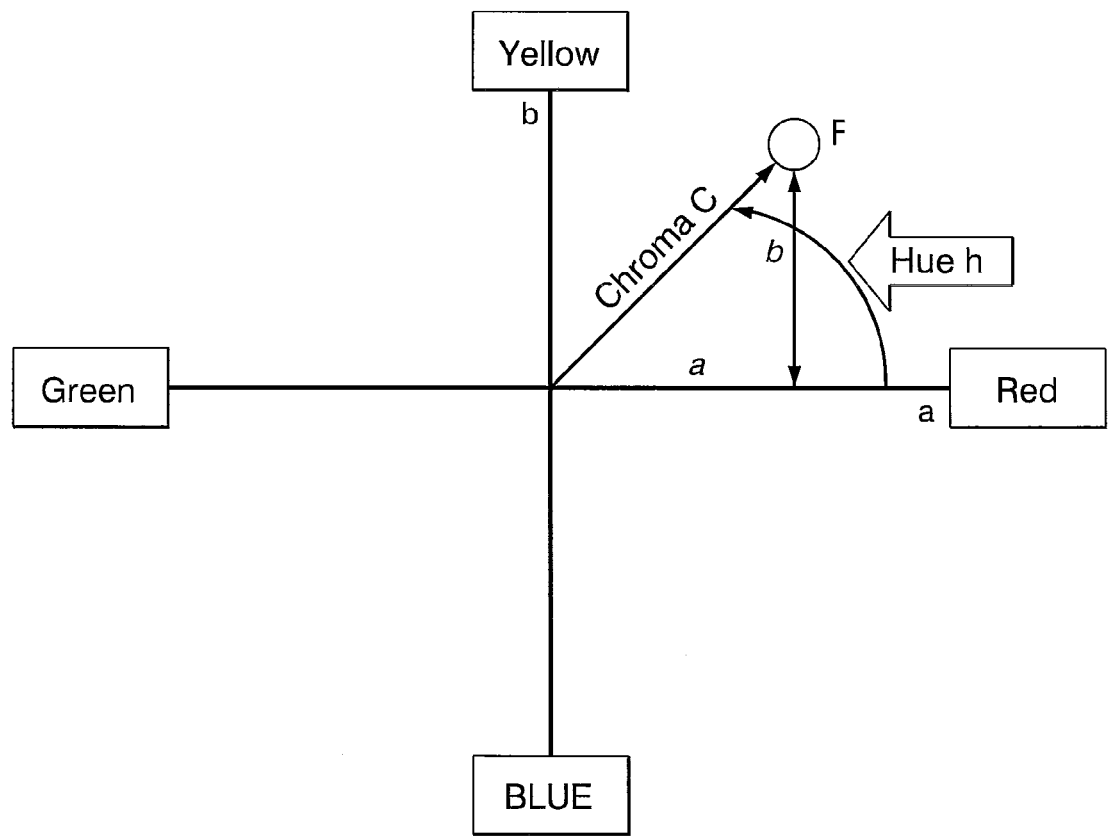
FIG. 1 is a graph of color coordinates in the CIELab color system.

According to one preferred variant of the invention, the cosmetic formulation comprises a silver-colored pigment having the following construction:

(a) nonmetallic platelet-shaped substrate,
(b) titanium oxide layer,
(c) ilmenite layer,
the pigment being obtainable by (i) applying an uncalcined titanium oxide/titanium hydroxide/titanium oxide hydrate layer to a nonmetallic, platelet-shaped, synthetic sub-strate,
(ii) applying an iron oxide/iron hydroxide/iron oxide hydrate layer to the uncalcined titanium oxide/titanium hydroxide/titanium oxide hydrate layer,
(iii) calcining the product obtained in step (ii), under reducing conditions.

After step (iii) the silver-colored pigment is obtained.

The problem of the invention is further solved by the use of the silver-colored pigment in a cosmetic formulation.

The term "cosmetically acceptable medium" encompasses, for example, nail varnish base systems, powder mixtures, W/O, O/W or W/Si emulsions, lotions, creams, wax preparations, saturated and unsaturated oils, inks, gels, liquid soap, curd soap or shampoos. These may be preliminary or semifinished products, such as tinting pastes, for example, or else the above-mentioned cosmetically acceptable media may be prepared from the corresponding cosmetic base materials, by methods known to the skilled person. The products in question may alternatively be end-use formulations which have already been pigmented and/or provided with fillers and/or auxiliaries, and into which the silver-colored pigments are incorporated subsequently.

By titanium oxide/titanium hydroxide/titanium oxide hydrate layer and iron oxide/iron hydroxide/iron oxide hydrate layer is meant, respectively, that a titanium oxide layer and/or titanium hydroxide layer and/or titanium oxide hydrate layer or an iron oxide layer and/or iron hydroxide layer and/or iron oxide hydrate layer may be present.

Ilmenite in the sense of this invention is understood to mean a compound with the stoichiometric composition $FeTiO_3$. Ilmenite may also be referred to as iron titanate.

The amount of iron compounds, calculated as elemental iron, in the silver-colored pigment is less than 5.0% by weight, preferably in a range from 1% by weight to 4.3% by weight, more preferably in a range from 1.4% by weight to 2.9% by weight and very preferably in a range from 1.5% by weight to 2.3% by weight, based in each case on the total weight of the pigment.

The amount of iron compounds, also referred to below as iron content, is understood in the sense of this invention to mean the complete content of iron compounds with different oxidation numbers in the pigment, the amounts of the entirety of detectable iron compounds being converted to arithmetically to elemental iron. This applies not only to the amount of iron compounds in the nonmetallic platelet-shaped synthetic substrates but also to the amount of iron compounds in the coating.

Unless otherwise indicated, the terms "layer" or "coating" are used interchangeably for the purposes of this invention.

The perception of a color as matt, pale or strong is critically dependent on its color saturation, referred to as the chroma or "coloredness". The chroma here is determined by the amount of gray that is present. The higher the gray content, the lower the color saturation.

Considering a point F in the CIELab color system, this point is defined via the three coordinates L* (lightness), a* (red-green axis) and b* (yellow-blue axis). The color coordinates a* and b* can also be expressed via polar coordinates C* (chroma) and h* (color angle, color locus), the definition being given as follows:

$$C^* = \sqrt{a^{*2} + b^{*2}}$$
$$h^* = \frac{180}{\pi} \cdot \arctan\left(\frac{b^*}{a^*}\right)$$

The chroma therefore corresponds to the length of the vector which points from the origin of the coordinate system to the point F that is to be defined. The lower the value of C*, the closer the point F to the achromatic region of the color coordinate system. The chroma, then, is the distance from the L* axis or gray axis which stands perpendicularly on the a*,b* plane (FIG. 1).

The silver-colored pigments are notable for low chroma values. With a measurement geometry of 110°, relative to the angle of emergence of the light irradiated at 45°, the chroma is $C^*_{110} \leq 2.4$, preferably in a range from $C^*_{110}=0$ to 2.3, more preferably in a range from $C^*_{110}=0.1$ to 2.1 and very preferably in a range from $C^*_{110}=0.2$ to 1.9. With a measurement geometry of 75°, relative to the angle of emergence of the light irradiated at 45°, the chroma is $C^*_{75} \leq 2.4$, preferably in a range from $C^*_{75}=0$ to 2.3, more preferably in a range from $C^*_{75}=0.1$ to 2.1 and very preferably in a range from $C^*_{75}=0.2$ to 1.9. The chroma values are measured using the Byk-mac instrument from Byk-Gardner, on the basis of coatings applied to metal panels. The panel-applied coatings were produced as described below in section IVa.

The silver-colored pigments are further notable for low values, lying close to the coordinate origin, for a* and b* in the CIELab color system. Preferred a* values, measured on the basis of panel-applied coatings using a Byk-mac from Byk-Gardner with the measurement geometries, relative to the angle of emergence of the light irradiated at 45°, of 15°, 25°, 45°, 75° and 110°, are within a range of at most +/−2; preferred b* values with these measurement geometries are within a range of at most +/−4.

If the silver-colored pigments are subjected to measurement on the basis of powder beds, they are notable even in the unoriented state for low values for a* and b*, and also, consequently, for low chroma values.

The nonmetallic platelet-shaped synthetic substrates of the silver-colored pigments are preferably substantially transparent, more preferably transparent, i.e. they are at least partly transmissive, preferably transmissive, for visible light.

The nonmetallic platelet-shaped synthetic substrates may be selected from the group consisting of synthetic mica platelets, glass platelets, $SiO_2$ platelets, $Al_2O_3$ platelets, synthetic boehmite platelets, polymer platelets, synthetic platelet-shaped substrates which comprise an inorganic-organic hybrid layer, and mixtures thereof. The nonmetallic platelet-shaped synthetic substrates are preferably selected from the group consisting of synthetic mica platelets, glass platelets, $Al_2O_3$ platelets and mixtures thereof. More preferably the nonmetallic platelet-shaped synthetic substrates are selected from the group consisting of synthetic mica platelets, glass platelets and mixtures thereof. Synthetic mica platelets are an especially preferred substrate.

Unlike nonmetallic platelet-shaped synthetic substrates, platelet-shaped natural substrates possess the drawback of possibly containing impurities due to intercalated extraneous ions. These impurities may alter the hue and/or reduce the lightness L*. Typical impurities in natural mica, for example, include nickel, chromium, copper, iron, manganese, lead, cadmium, arsenic and/or antimony and/or compounds thereof, which may give the natural mica, for example, a coloration.

The amount of the aforementioned extraneous ions, with the exception of iron, calculated as elemental metal, in the nonmetallic platelet-shaped synthetic substrate is preferably in each case less than 15 ppm, more preferably less than 10 ppm, based in each case on the total weight of the substrate.

The iron content, calculated as elemental iron, of the nonmetallic platelet-shaped synthetic substrates ought more particularly to be extremely low and ought preferably to be less than 0.20% by weight, more preferably in a range from 0.01% by weight to 0.20% by weight, with further preference in a range from 0.03% by weight to 0.19% by weight and with particular preference in a range from 0.04% by weight to 0.18% by weight, based in each case on the total weight of the substrate.

The iron content of the nonmetallic platelet-shaped synthetic substrates is determined preferably via X-ray fluorescence (XRF) analysis. For such analysis, the nonmetallic platelet-shaped synthetic substrates are admixed with lithium tetraborate, melted in an oxidizing atmosphere and subjected to measurement in the form of a homogeneous glass tablet. The instrument used was the Advantix ARL from Thermo Scientific.

As well as the color neutrality of the nonmetallic platelet-shaped synthetic substrate, its lightness as well shares responsibility for the visual impression given by pigments based thereon. The lightness L* of the nonmetallic platelet-shaped synthetic substrates, determined by diffuse color measurement of the respective powder beds using a CR 310 colorimeter from Konica Minolta, is preferably ≥90, more preferably ≥92 and very preferably ≥95.

A further difference between nonmetallic platelet-shaped natural and synthetic substrates is that as a result of their production the surface of platelet-shaped natural substrates is not ideally smooth but may instead have irregularities, such as steps, for example. Nonmetallic platelet-shaped synthetic substrates generally have smooth surfaces and also a uniform thickness within one individual substrate particle and also, preferably, over the entirety of all of the substrate particles. The surface therefore affords only few scattering centers for incident and reflected light, and consequently, after these platelet-shaped substrates have been coated, allows pigments which are more glossy than those with, for example, platelet-shaped natural mica as their substrate.

Furthermore, contaminations due to heavy metals, especially in cosmetic formulations, are unwanted in the interest of the consumer. Elevated levels of lead in cosmetic formulations, in particular, are unwanted. Color additives are monitored by the FDA for their lead content and may not exceed a limiting value of 20 µg/g.

Other cosmetic ingredients are subject to the responsibility of the manufacturers with regard to their lead content (Nancy M. Hepp, William R. Mindak, John Cheng, J. Cosmet. Sci., 60, 405-414 (July/August 2009)).

In one embodiment the lead content of the synthetic mica platelets which can be used as substrate is preferably less than 5 ppm, more preferably in a range from 0.05 ppm to 3 ppm and very preferably in a range from 0.03 ppm to 2 ppm. Most preferably the synthetic mica platelets contain no lead and no lead compounds.

In another embodiment, the silver-colored pigments based on synthetic mica platelets have a total lead content of preferably less than 10 ppm, more preferably from a range from 0.0 ppm to less than 9 ppm, with further preference from a range from 0.0 ppm to less than 8 ppm, more preferably still from a range from 0.1 ppm to less than 7 ppm, and very preferably from a range from 0.1 ppm to less than 6.5 ppm.

The lead content of the synthetic mica platelets and also of the silver-colored pigments based thereon is determined in this context via solids graphite tube atomic absorption spectrometry. The instrument used is preferably a ZEENIT 650 with SSA 600 solids sampler from Analytik Jena.

In another embodiment, the nonmetallic platelet-shaped synthetic substrates may have a refractive index from a range from 1.55 to 1.70, preferably from a range from 1.58 to 1.68 and more preferably from a range from 1.59 to 1.65.

Where the nonmetallic platelet-shaped synthetic substrate consists of glass platelets, preference is given in the context of this invention to using those which are produced in accordance with the processes described in EP 0 289 240 A1, WO 2004/056716 A1 and WO 2005/063637 A1. The glass platelets which can be used as substrate may have a composition, for example, in accordance with the teaching of EP 1 980 594 B1.

Where the nonmetallic platelet-shaped synthetic substrate consists of synthetic mica, this mica may have various chemical compositions and may differ in its optical properties among others. Differences in the platelet-shaped substrate may also be apparent in the pigment based thereon. The choice of suitable synthetic platelet-shaped mica as the substrate for coating is therefore highly important for the visual appearance of the resulting pigments.

Synthetic mica platelets as substrate are preferably, in the context of this invention, fluorophlogopite of the general formula $X_1Y_{2-3n}(Z_4O_{10})F_2$, where X may be selected from the group consisting of $K^+$, $Na^+$, $Li^+$ and/or $Ca^{2+}$, Y may be selected from the group consisting of $Mg^{2+}$ and/or $Zn^{2+}$, and Z may be selected from the group consisting of $Si^{4+}$ and/or $Al^{3+}$, and n is or 1. It is particularly preferred to use fluorophlogopite of the formula $KMg_3AlSi_3O_{10}F_2$, $KMg_2\frac{1}{2}(Si_4O_{10})F_2$ or $NaMg_2\frac{1}{2}(Si_4O_{10})F_2$ as nonmetallic platelet-shaped substrate. Especially preferred here is fluorophlogopite of the formula $KMg_3AlSi_3O_{10}F_2$.

Platelet-shaped fluorophlogopite is a substrate with high temperature stability and with chemical stability, and is extremely suitable for the purposes of the present invention.

The production of the synthetic mica can be tailored, with the consequence that the resultant synthetic mica platelets have extremely few defects.

The synthetic mica platelets used with preference as nonmetallic platelet-shaped synthetic substrate preferably comprise, according to X-ray fluorescence analysis, the constituents mentioned in Table 1, in the ranges listed.

TABLE 1

Preferred compositions of platelet-shaped synthetic mica according to X-ray fluorescence (XRF) analysis Composition of synthetic mica platelets, figures in % by weight, based in each case on the total weight of the synthetic mica platelets

| | |
|---|---|
| $SiO_2$ | 38 to 46 |
| $Al_2O_3$ | 10 to 14 |
| $K_2O$ | 9 to 13 |
| $Fe_2O_3$ | 0.01 to 0.25 |
| MgO | 26 to 34 |
| MnO | 0 to 0.05 |
| $Na_2O$ | 0 to 13 |

Even in the event of minor deviations from the figures given by way of example in Table 1, it is possible to obtain the silver-colored pigments for use in the cosmetic formulation of the invention. It is self-evident that the fraction of coloring components here ought not to deviate significantly from the figures given in Table 1, and that no other coloring components, or only insubstantial traces of coloring components, may be present in the substrate.

Preferred magnesium oxide values for the silver-colored pigments according to X-ray fluorescence analysis are situated in a range from 10% to 30% by weight, more preferably in a range from 13% to 27% by weight, very preferably in a range from 17% to 23% by weight, based in each case on the total weight of the pigments.

Applied to the nonmetallic platelet-shaped synthetic substrates is at least one high-index layer having a refractive index of n>2.0, preferably of n>2.2. The at least one high-index layer has a metal oxide layer and/or a metal hydroxide layer and/or a metal oxide hydrate layer or consists thereof.

For the formation of an ilmenite layer, the nonmetallic platelet-shaped synthetic substrate must comprise not only at least one titanium oxide layer but also at least one adjacent iron oxide layer and/or at least one titanium hydroxide layer and at least one adjacent iron hydroxide layer and/or at least one titanium oxide hydrate layer and at least one adjacent iron oxide hydrate layer. Under reducing conditions, preferably in the presence of forming gas ($N_2/H_2$), and at temperatures of at least 500° C., the reaction to form ilmenite takes place at the interface between titanium oxide layer and iron oxide layer or between titanium oxide hydrate layer and iron oxide hydrate layer or between titanium hydroxide layer and iron hydroxide layer. In the boundary region there is a partial penetration of both layers, and ilmenite is formed. In the resultant silver-colored pigments, accordingly, a gradient is found from a layer consisting exclusively of titanium oxide to a layer consisting exclusively of ilmenite. In the layer which after subsequent calcining comprises titanium oxide, there may additionally be small amounts of titanium suboxide species that are formed under the reducing conditions, the fraction thereof being sufficiently small as not to affect the appearance of the silver-colored pigments.

In accordance with one preferred embodiment of the invention, the fraction of titanium oxide in the coating decreases from the substrate-facing side to the substrate-remote side of the titanium oxide layer. Accordingly, the ilmenite layer as well has a concentration gradient which decreases in the substrate direction.

In order to obtain the silver-colored pigments, the titanium dioxide needed for formation of ilmenite may be present in the anatase or rutile form. In one preferred embodiment, the titanium dioxide is in the rutile form. The rutile form may be obtained by applying a layer of tin dioxide to the platelet-shaped transparent substrate that is to be coated, before the titanium dioxide layer is applied, for example.

Titanium dioxide in the rutile modification crystallizes on this layer of tin dioxide. The tin dioxide here may take the form of a separate layer, in which case the layer thickness may amount to a few nanometers, for example less than 10 nm, more preferably less than 5 nm, more preferably still less than 3 nm.

In one particularly preferred embodiment, the reaction to form ilmenite takes place at the interface of the titanium oxide hydrate/titanium hydroxide layer and iron oxide hydrate/iron hydroxide layer; in other words, a pigment coated with titanium oxide hydrate and/or with titanium hydroxide is coated with iron oxide hydrate and/or iron hydroxide, without prior calcining and without prior optional isolation, and is subsequently calcined or treated at elevated temperature under reducing conditions.

The silver-colored pigments for use in the cosmetic formulation of the invention are notable for a neutral or pure silver hue without color tinge, for example without a weakly blue, greenish, reddish or golden coloration, which might give a visual suggestion of a pearlescent pigment. Neutral or pure silver hues are characteristic of metallic effect pigments, such as aluminum effect pigments, for example. The silver-colored pigments are therefore devoid of the incidence of interference color and complementary color, which is characteristic of pearlescent pigments and which occurs particularly on a white substrate, depending on the viewing angle. The silver-colored pigments also lack the depth gloss typical of pearlescent pigments.

If the ilmenite-forming reaction is incomplete, and hence iron(III) oxide is still present after the reduction, then the resulting pigments possess a brownish coloration. This deviation from a neutral silver hue can be seen with the naked eye. In one preferred embodiment, the silver-colored pigments have an iron(III) oxide content of less than 0.5% by weight, more preferably from a range from 0.0% by weight to 0.4% by weight, more preferably still of less than 0.3% by weight, with particular preference from a range from 0.1% by weight to 0.3% by weight, based in each case on the total weight of the pigment.

Because of the ilmenite layer, typical properties of pearlescent pigments such as depth gloss and transparency are lost. Instead, the silver-colored pigments have characteristic features of metallic effect pigments, such as the outstanding opacity.

Comparing the silver-colored pigments with silver-colored pearlescent pigments without an ilmenite layer in terms of their optical properties, it is found that the silver-colored pigments, even when the ilmenite content is very low, evoke the visual impression of an aluminum effect pigment. The transparency which is present in pearlescent pigments without an ilmenite layer gives way, with pigments having an ilmenite layer, to the opacity characteristic of metallic effect pigments, and the soft gloss, which appears to come from deep down, is replaced by the hard metallic luster.

The light/dark flop as well that characterizes metallic effect pigments and is especially pronounced for aluminum effect pigments can be observed to an increased extent in the silver-colored, ilmenite-coated pigments. It is therefore preferred for the silver-colored pigments to be not transparent and to have preferably a metallic light/dark flop.

Since the silver-colored pigments have a metallic appearance by virtue of the ilmenite layer, and yet neither a metallic core nor a metallic layer is present on the nonmetallic platelet-shaped synthetic substrate, the outstanding chemical stability and the high temperature stability that characterize pearlescent pigments are retained. Of course, chemically stable and temperature-stable metallic effect pigments are available commercially as well, but in contrast to pearlescent pigments they must be subjected to a costly and inconvenient aftertreatment in order to attain these stability qualities.

The cosmetic formulation of the invention uses a new pigment category which in terms of chemical and mechanical stability is similar to the pearlescent pigments, but in terms of its optical properties is remarkably similar to metallic effect pigments. The silver-colored pigments for use in the cosmetic formulation of the invention are described in DE 10 2011 001 579, which is hereby incorporated by reference.

The silver-colored pigments for use in the cosmetic formulation of the invention have proven extremely temperature-stable and also corrosion-stable and chemically stable.

The chemicals stability of the silver-colored pigments is verified on the basis of coatings applied to metal panels and exposed to the action of an acid or alkali. The corrosion resistance of the silver-colored pigments was determined on the basis of its gassing behavior in an aqueous carbomer gel system.

Whether the silver-colored pigments for use in the cosmetic formulation of the invention possess the desired temperature stability is determined by storage of the pigments at temperatures of 100° C. to 200° C. Following storage, the pigments are investigated for possible color changes by means of doctor-blade drawdowns.

The color-neutral, silver-colored pigments with metallic appearance can be obtained, on the basis of nonmetallic platelet-shaped synthetic substrates having above-identified properties, surprisingly even in the presence of a very thin ilmenite layer, having an average layer thickness from a range from 1 to 20 nm, preferably 6 to 15 nm. Surprisingly, the formation of a thicker ilmenite layer is unnecessary. Hence the formation of a very thin ilmenite layer at less than 20 nm is sufficient to give a silver-colored pigment which is similar in its optical properties to a metallic effect pigment, more particularly to an aluminum effect pigment.

In the absence of further iron components necessary as for ilmenite formation, an iron/titanium weight ratio, calculated as the ratio of elemental iron to elemental titanium, from a range from 0.1 to 0.25 may be sufficient in order to suppress the characteristic pearlescence. Following ilmenite coating, the silver-colored pigments are identical in their optical properties to metallic effect pigments, while functional properties of pearlescent pigments are retained. Accordingly, the silver-colored pigments of the present invention can be employed ideally in applications which do require a metallic appearance but not a metallic effect pigment.

An iron/titanium weight ratio, calculated as the ratio of elemental iron to elemental titanium, of less than 0.1 would impair the opacity of silver-colored pigments, while an iron/titanium weight ratio of more than 0.25 makes virtually no additional contribution to the opacity.

For the purpose of determining the iron/titanium weight ratio, the titanium oxide content as determined by X-ray fluorescence measurements is converted arithmetically to elemental titanium. The amount of iron compounds is likewise converted arithmetically to elemental iron. As already mentioned when defining the iron content, the titanium content as well describes the entirety of all of the detectable titanium compounds in the pigment, converted arithmetically to elemental titanium.

The iron/titanium weight ratio of the silver-colored pigments is dependent on the particle size of the pigment and/or on the average thickness of the nonmetallic platelet-shaped synthetic substrate. Both the iron content and the titanium content are therefore dependent on the average particle size $D_{50}$ and on the average thickness of the nonmetallic platelet-shaped synthetic substrates to be coated. The optical layer thickness of the layer surrounding the platelet-shaped nonmetallic synthetic substrate is responsible for the color of the resulting pigments.

A coating with titanium dioxide with an optical layer thickness of 140 nm, for example, produces silver-colored pearlescent pigments. However, the amount of, for example, titanium dioxide that is necessary for achieving this optical layer thickness is dependent on the average particle size $D_{50}$ and average thickness of the nonmetallic platelet-shaped substrates to be coated. A silver-colored pearlescent pigment based on natural mica and having an average particle size $D_{50}$ of approximately 20 μm (e.g. Pearlescent Pigment Prestige Silver Star, Sudarshan Chemical Industries Limited, India) has a titanium dioxide content of approximately 30% by weight, while a corresponding pearlescent pigment with an average particle size $D_{50}$ of approximately 10 μm (e.g. Pearlescent Pigment Prestige Silk Silver Star, Sudarshan Chemical Industries Limited, India) has a titanium dioxide content of approximately 37% by weight.

In order to define, for the silver-colored pigments, an iron/titanium weight ratio which is independent of the average particle size $D_{50}$ and/or average thickness of the nonmetallic platelet-shaped synthetic substrate, the fraction of the coating is taken into account when determining the iron/titanium weight ratio, in accordance with formula (I):

$$\frac{\text{Iron content (\% by weight)}}{\text{Titanium content (\% by weight)}} \cdot \text{Fraction of the coating (\% by weight)}. \quad (I)$$

The fraction of the coating (% by weight) is defined from the total weight of the pigment minus the fraction of the substrate (% by weight). The iron content is defined as the entirety of all of the detectable iron compounds in the pigment, converted arithmetically to elemental iron. Similarly, the titanium content is defined as the entirety of all of the detectable titanium compounds in the pigment, converted arithmetically to elemental titanium.

The iron/titanium weight ratio in accordance with formula (I) for the silver-colored pigments is situated preferably in a range from 1 to 8, more preferably in a range from 2 to 7.5, very preferably in a range from 2.5 to 7, and very preferably indeed in a range from 3 to 6.

The opacity of the silver-colored pigments was determined on the basis of the lightness values L*, measured using the Byk mac instrument from Byk-Gardner, of coatings applied to black-white opacity charts (Byko-Chart 2853, Byk-Gardner). For this purpose, the lightness values on the black and white background of the black-white opacity chart were determined with a measurement geometry of 110°, relative to the angle of emergence of the light irradiated at 45°, and the ratio thereof was formed. In the context of this invention, values from $L^*_{110,black}/L^*_{110,white}$ of more than 0.5 are considered to be opaque.

The opacity of the silver-colored pigments is additionally dependent on their overall thickness. The thicker the substrate of the silver-colored pigments, the lower their opacity. For example, silver-colored pigments which are based on glass platelets having a thickness of more than 1 μm give a lower opacity than silver-colored pigments which possess as their substrate platelet-shaped synthetic mica having a thickness of 400 nm. This can be explained by the fact that in a defined amount of pigment, of 1 g pigment, for example, the number of individual pigments in the case of thinner pigments is of course greater than would be the case for thicker pigments. This smaller pigment count is responsible, in an application, for a comparatively lower opacity.

In contrast to transparent pearlescent pigments, opaque metallic effect pigments are notable for a higher covering power. The covering power of the silver-colored pigments is comparable with that of metallic effect pigments, more particularly aluminum effect pigments.

At the specular angle, metallic effect pigments exhibit the typical metallic luster, which is lost outside the specular angle. Outside the specular angle, applications comprising metallic effect pigments appear less glossy and dark. This effect is also observed with the silver-colored pigments.

Following application to, for example, a metal panel, and drying, a coating material which comprises the silver-colored pigments exhibits a substantially angle-dependent gloss effect or what is called a light/dark flop. This change in lightness is described by the flop index. The flop index is defined in accordance with Alman as follows (S. Schellenberger, M. Entenmann, A. Hennemann, P. Thometzek, Farbe and Lack, 04/2007, p. 130):

$$\text{Flop index} = 2.69 \cdot (L_{E1} - L_{E3})^{1.11} / L_{E2}^{0.86}$$

where $L_{E1}$ is the lightness of the near-specular measuring angle (E1=15° relative to the specular angle), $L_{E2}$ is the lightness of the measuring angle between near-specular and far-specular angle (E2=45° relative to the specular angle) and $L_{E3}$ is the lightness of the far-specular measuring angle (E3=110° relative to the specular angle). The larger the numerical value of the flop index, the more greatly the light/dark flop is expressed.

Given a comparable particle size distribution and more particularly given a comparable average particle size $D_{50}$, the flop index of the silver-colored pigments is virtually identical with that of an aluminum effect pigment.

The ratio of flop index to $D_{50}$ describes the angle-dependent change in lightness of the silver-colored pigments as a function of the average particle size $D_{50}$ of the respective pigment. The flop index/$D_{50}$ ratio is situated preferably in a range from 0.5 to 1.9, more preferably in a range from 0.6 to 1.8 and very preferably in a range from 0.7 to 1.7.

The visual appearance of the pigments cannot be reproduced by simple mixing of a conventional silver-colored pearlescent pigment with diverse dyes/pigments such as carbon black, for example. If opaque dyes/pigments are used, the gloss and the effect of the silver-colored pearlescent pigment are lost. When transparent dyes/pigments are used, therefore, it is impossible to achieve opacity.

When applied coatings which comprise the silver-colored pigments for use in the cosmetic formulation of the invention are compared with applied coatings which comprise commercial silver-colored pearlescent pigments, the different visual impression is immediately evident to a viewer.

Applied coatings which comprise exclusively the silver-colored pigments produce a visual impression of pure or color-neutral silver, i.e. without additional color impressions.

Furthermore, these applied coatings exhibit a metallic appearance and an extraordinary glitter effect.

Figure 2:
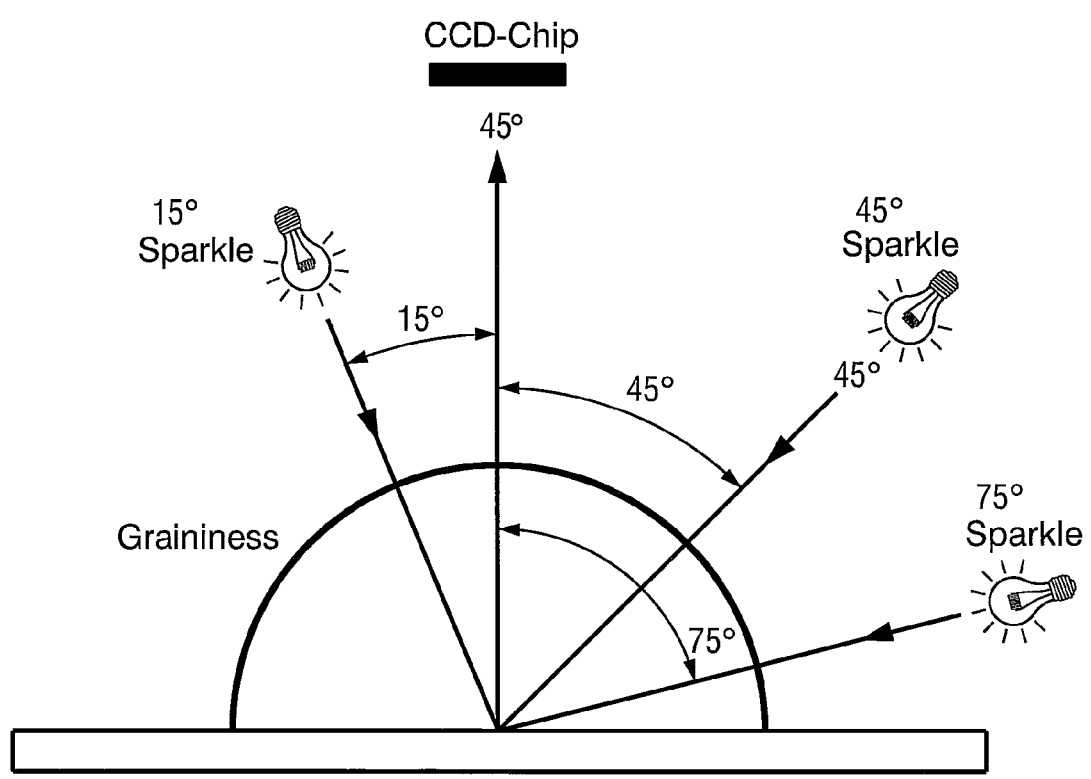
FIG. 2 is a diagram of Byk mac effect measurement geometries (Byk-Gardner, catalog "Qualitätskontrolle für Lacke and Kunststoffe [Quality Control for coatings and plastics]" 2011/2012, p. 97)

In order to describe objectively the optical effect of the silver-colored pigments, multiangle color measurements and effect measurements were carried out using a BYK-mac (Byk-Gardner) on the basis of coatings applied to metal panels. The BYK-mac measures the total color impression at different viewing angles and light conditions. The multiangle color measurement serves here to capture and describe the light/dark flop and/or color flop of coating materials provided with effect pigments. The measurement geometries (−15°), +15°, 25°, 45°, 75°, 110° are measured relative to the angle of emergence of the light irradiated at 45°. To simulate effect changes upon direct and diffuse illumination, glitter effect and graininess are simultaneously monitored with the help of a high-resolution CCD camera. The glitter effect, caused by the reflecting ability of the individual effect pigments, is only perceived upon direct solar irradiation, and changes depending on the illumination angle. For this reason, the Byk-mac illuminates the sample with very bright LEDs at three different angles (15°/45°/75°, FIG. 2). The CCD camera takes an image perpendicularly to the surface in each case. The images are analyzed using image processing algorithms, using the histogram of the lightness stages as a basis for calculating the glitter parameters. In order to ensure better differentiation, the glitter effect can be described by a two-dimensional system, the glitter area S_a and the glitter intensity S_i, which can also be summarized in a one-dimensional value, the glitter degree S_G (Byk-Gardner, catalog "Qualitätskontrolle für Lacke and Kunststoffe" [Quality control for coatings and plastics] 2011/2012, pp. 97/98).

The measured glitter area and glitter intensity is influenced by the orientation of the pigments. A pigment with good alignment, in other words aligned largely plane-parallel to the substrate, has the highest measurement values at an illumination geometry of 15°, in a comparison of the glitter measurement values S_a, S_i and S_G obtained in the illumination geometries 15°, 45° and 75°, since a large part of the pigments directly reflects the irradiated light. With an illumination geometry of 45°, the irradiated light is largely reflected directly and is thus perceived as a relatively weak glitter effect when observed perpendicularly to the application. The glitter effect observed with this illumination geometry is attributable partly to pigments with incorrect orientation, i.e. without plane-parallel orientation, which are able to divert the light irradiated at 45° in the direction of the detector. With an illumination geometry of 75°, no glitter effect, or only a weak glitter effect, is perceived perpendicularly to the application. This effect is in turn caused by incorrectly arranged pigments.

Consequently, a well-oriented pigment has the greatest glitter effect at 15°; the minimum glitter effect, relative to the 15° measurement, is observed at 75°. In the case of a poorly oriented pigment, the differences of the measurement values observed at 15°, 45° and 75° illumination geometry are smaller, since light is always reflected in the direction of the detector as a result of the incorrect orientation.

The one-dimensional glitter degree S_G is critical to the visual impression. The higher the numerical value of S_G, the higher the glitter effect that can be perceived by the eye. In a two-dimensional representation, the glitter degree S_G can be divided into the components of glitter intensity S_i and glitter area S_a. Since both components have a critical influence on the glitter degree S_G, it may be the case that a pigment in the measurement geometries 15°, 45° and 75° exhibits virtually the same glitter degree S_G, despite the fact that the numerical values of S_a and S_G at the angles considered increase or decrease significantly.

In contrast to silver-colored pearlescent pigments based, for example, on natural mica, which are different neither in layer construction nor in particle size from the silver-colored pigments for use in the cosmetic formulation of the invention, these silver-colored pigments, at a measurement geometry of 15°, exhibit far higher values for glitter intensity S_i and glitter area S_a. Accordingly, the visual difference that is visible for a viewer can also be demonstrated by measurement.

With an average particle size $D_{50}$ of the silver-colored pigments from a range from 15 to 25 μm, the glitter intensity S_i with a measurement geometry of 15°, relative to the angle of emergence of the light irradiated at 45°, is preferably >10, more preferably >11 and very preferably >12. With an average particle size $D_{50}$ of the silver-colored pigments from a range from 5 to <15 μm, the glitter intensity S_i with a measurement geometry of 15°, relative to the angle of emergence of the light irradiated at 45°, is preferably >5, more preferably >6 and very preferably >7.

As well as the glitter intensity S_i, the flop index as well, as already mentioned, is dependent on the average particle size $D_{50}$. A change in the average particle size $D_{50}$ has consequences to a particular degree for these two numerical characteristics. The product of flop index and glitter intensity S_i as a function of the average particle size $D_{50}$, in accordance with formula (II)

$$\text{Flop intensity } (F_i) = \frac{\text{Flop index} \cdot S\_i}{D_{50}}, \qquad (II)$$

is defined as flop intensity ($F_i$) and impressively demonstrates the visible difference between the silver-colored pigments of the invention and pigments that are available commercially. The value for the product of flop index and glitter intensity as a function of the average particle size $D_{50}$, in accordance with formula (II), is preferably at least 10. The higher this value, the more glittery and metallic the pigment appears to a viewer.

For the preparation of the silver-colored pigments, the nonmetallic platelet-shaped synthetic substrate is preferably suspended in water. To the suspension is added, preferably at a temperature from a range from 50° C. to 100° C. and preferably at a pH which is held constant and which comes from a range from 1.4 to 4.0, preferably a water-soluble inorganic tin compound and then preferably a water-soluble inorganic titanium compound. When the addition of the water-soluble titanium compound is at an end, the suspension then obtained is preferably stirred for at least 30 minutes, and then preferably a water-soluble inorganic iron compound is added. After the end of the reaction, the nonmetallic platelet-shaped synthetic substrate, which is now covered with a titanium oxide hydrate/titanium hydroxide layer and with an iron oxide hydrate/iron hydroxide layer, is separated off, washed if desired, optionally dried and subjected preferably at temperatures in the range from 500° C. to 1200° C. under reducing conditions, more preferably in the presence of forming gas ($N_2/H_2$), to thermal treatment or calcining. The thermal treatment or calcining is carried out preferably until the iron oxide hydrate/iron hydroxide present has undergone virtually complete, preferably complete, reaction to form ilmenite.

According to WO 2004/099319 A2, it is extremely important that in the preparation of ilmenite-containing pigments, the water-soluble inorganic titanium compound and the water-soluble inorganic iron compound are applied simultaneously to a platelet-shaped substrate which may have already been coated. It is additionally noted that the simultaneous addition of both components allows pigments to be obtained that have optical properties improved relative to the prior art.

In the context of this invention, however, it has surprisingly been found that when nonmetallic platelet-shaped synthetic substrates are used, even in the case of successive addition, as known from the prior art, of the water-soluble inorganic titanium compound and iron compound, it is possible to obtain highly lustrous silver-colored pigments with a high glitter intensity, a pronounced light/dark flop, and a high hiding power, which do not have the disadvantages referred to in WO 2004/099319 A2.

It has further proven exceptionally advantageous, in contrast to EP 0 246 523 A2, for example, to add the water-soluble inorganic iron compound in situ and not to use as starting material a pearlescent pigment which is coated with titanium dioxide and has already been calcined. Given identical layer construction, consisting for example of a titanium dioxide layer and an ilmenite-containing layer, the difference in process between calcining the water-soluble inorganic iron compound prior to application and continuing the coating operation in situ is manifested in the chemicals stability. The silver-colored pigments which are produced without prior calcining are significantly more stable toward acid and alkali than pearlescent pigments produced in accordance with EP 0 246 523 A2, starting from a calcined pigment. The silver-colored pigments are also superior in chemicals stability to pearlescent pigments obtained by simultaneous addition of a water-soluble inorganic titanium compound and a water-soluble inorganic iron compound. The application of the iron oxide hydrate/iron hydroxide layer to the uncalcined titanium oxide hydrate/titanium hydroxide layer is essential for the structural difference of the pigments relative to the pearlescent pigments known from the prior art.

The inventors assume that when uncalcined titanium oxide hydrate/titanium hydroxide layers are used, the iron oxide hydrate/iron hydroxide layer that is applied subsequently is able to penetrate to a greater extent into the pores of the adjacent titanium oxide hydrate/titanium hydroxide layer. This improved penetration produces a virtually complete conversion to ilmenite, not only directly at the interface.

When pearlescent pigments which have already been calcined and are covered with titanium dioxide are used, such penetration is not possible. Moreover, calcined titanium dioxide is much slower to react than titanium oxide hydrate or titanium hydroxide. Even at low layer thicknesses, therefore, the conversion to ilmenite is usually incomplete. This is manifested particularly in a poorer chemicals stability.

The silver-colored pigments for use in the cosmetic formulation of the invention are not multilayer pearlescent pigments whose layer construction comprises a high-index, low-index, high-index coating.

For emulating the optical properties of an aluminum effect pigment, the nonmetallic platelet-shaped synthetic substrate ought preferably to have properties as follows. In the case of one preferred variant of the invention, the nonmetallic platelet-shaped synthetic substrate meets all of the properties set out hereinbelow in relation to extraneous-ion content, substrate thickness, and lightness.

In order, besides the perceived silvery color in the pigments, to avoid a color tinge or coloration, the nonmetallic platelet-shaped synthetic substrate ought to have only negligible quantities of intercalated extraneous ions which may alter the hue. The nonmetallic platelet-shaped synthetic substrate is preferably substantially colorless, preferably colorless.

The silver-colored pigments are preferably nonmagnetic or only slightly magnetic. Furthermore, the silver-colored pigments are not electrically conductive.

The average thickness of the substrate is preferably selected such that the silver-colored pigments for use in the cosmetic formulation of the invention have a high opacity. The average thickness of the nonmetallic platelet-shaped synthetic substrates to be coated is situated preferably in a range from 50 nm to 5000 nm, more preferably in a range from 60 nm to 3000 nm, and very preferably in a range from 70 nm to 2000 nm.

In one embodiment, the average thickness for glass platelets as the substrate to be coated is situated preferably in a range from 750 nm to 1500 nm. Glass platelets of this kind are available commercially on a broad basis. Further advantages are offered by thinner glass platelets. Thinner substrates lead to a lower overall layer thickness of the silver-colored pigments. Accordingly, preference is likewise given to glass platelets whose average thickness is situated in a range from 100 nm to 700 nm, more preferably in a range from 150 nm to 600 nm, very preferably in a range from 170 nm to 500 nm, and especially preferably in a range 200 nm to 400 nm.

In another embodiment, the average thickness for synthetic mica as the nonmetallic platelet-shaped substrate to be coated is situated preferably in a range from 100 nm to 700 nm, more preferably in a range from 120 nm to 600 nm, very preferably in a range from 140 nm to 500 nm, and especially preferably in a range from 150 nm to 450 nm.

Where nonmetallic platelet-shaped synthetic substrates below an average thickness of 50 nm are coated with, for example, high-index metal oxides, the resulting pigments are extremely fragile, and may break apart even on incorporation into the application medium, entailing in turn a significant reduction in luster. Moreover, the coating times for these thin substrates with, for example, high-index metal oxides are very long, owing to the high specific surface areas (surface area per unit weight of pigment) of these nonmetallic platelet-shaped synthetic substrates, and this causes high production costs. Above an average substrate thickness of 5000 nm, the pigments may become too thick overall. This may be associated with a poorer specific opacity, i.e. area covered per unit weight of pigment, and also with a lower level of plane-parallel orientation in the application medium. The result of a poorer orientation, in turn, is a reduced luster.

The average thickness of the nonmetallic platelet-shaped synthetic substrate is determined on the basis of a cured varnish film in which the pigments are oriented substantially plane-parallel to the substrate. For this purpose, a polished section of the cured varnish film is examined under a scanning electron microscope (SEM), and the thickness of the nonmetallic platelet-shaped synthetic substrate is determined for 100 pigments and averaged.

It is preferred, furthermore, for the nonmetallic platelet-shaped synthetic substrate to have a high lightness, expressed as $L^*$ value, of at least 90, more preferably of at least 92, more preferably still of at least 95. The lightness here is determined by diffuse colorimetry on the basis of powder beds.

The surface of the nonmetallic platelet-shaped synthetic substrate, furthermore, is preferably very smooth and free from air inclusions, abrupt discontinuities, cracks and/or other constituents that give rise to light scattering.

More particularly, synthetic mica platelets which comprise, within the stated limits, the composition set out in Table 1 have proven to be a highly suitable nonmetallic substrate for producing the silver-colored pigments with metallic appearance for use in the cosmetic formulation of the invention.

The silver-colored pigments may have any desired average particle size $D_{50}$. The $D_{50}$ values of the silver-colored pigments are situated preferably in a range from 3 to 80 μm. The silver-colored pigments more preferably have a $D_{50}$ value from a range from 5 to 63 μm, with particular preference from a range from 7 to 56 μm, and especially preferably from a range from 9 to 49 μm.

The $D_{10}$ values of the silver-colored pigments are situated preferably in a range from 1 to 25 μm. The silver-colored pigments more preferably have a $D_{10}$ value from a range from 2 to 21 μm, very preferably from a range from 3 to 18 μm, and especially preferably from a range from 4 to 14 μm.

The $D_{90}$ values of the silver-colored pigments are situated preferably in a range from 6 to 250 μm. The silver-colored pigments more preferably have a $D_{90}$ value from a range from 15 to 210 μm.

The $D_{10}$, $D_{50}$, and $D_{90}$ values of the cumulative frequency distribution of the volume-averaged size distribution function as obtained by laser diffraction methods indicate that 10%, 50%, and 90%, respectively, of the silver-colored pigments have a diameter which is the same as or less than the respective figure indicated. In this case the size distribution curve of the pigments is determined using an instrument from Malvern (instrument: MALVERN Mastersizer 2000) in accordance with manufacturer instructions. The scattered-light signals are evaluated by the Fraunhofer method.

The silver-colored pigments may optionally be provided with at least one external protective layer, further enhancing the light stability and/or chemical stability of the pigment. The external protective layer may also be an aftercoating which facilitates the handling of the silver-colored pigments during incorporation into different media.

The external protective layer may also be organic-chemically modified on the surface. For example, one or more, preferably cosmetically approved, silanes may be applied to this external protective layer. The silanes may be alkyl silanes having branched or unbranched alkyl radicals of 1 to 24 C atoms, preferably 6 to 18 C atoms.

In a further-preferred embodiment, the silane without a functional binding group is an alkyl silane. The alkyl silane preferably has the formula $R_{(4-z)}Si(X)_z$. In this formula, z is an integer from 1 to 3, R is a substituted or unsubstituted, unbranched or branched alkyl chain of 10 to 22 C atoms, and X is a halogen and/or alkoxy group. Preferred alkyl silanes are those with alkyl chains of at least 12 C atoms. R may also be joined cyclically to Si, in which case z is usually 2.

For the incorporation of pigments aftercoated with silanes and/or provided with an external protective layer into cosmetic formulations, it is necessary to ensure that the silane in question and/or the material of the external protective layer meets the specific regional requirements of the cosmetics ordinances. Furthermore, there must be an INCI name available. Common examples of such are organosilanes with the INCI names: triethoxycaprylylsilane, stearyl triethoxy-silane, polymethylsilsesquioxane/trimethylsiloxy-silicate, sodium carboxyethylsilanetriol.

In another embodiment the silver-colored pigments may be covered with at least one organic aftercoating which is applied in a way known to the skilled person.

Preferred methods for aftercoating include for example:

PEG silicone coating, for example the "AQ" modification, available from LCW, chitosan coating, for example the "CTS" modification, available from LCW, triethoxycaprylylsilane coating, for example the "AS" modification, available from LCW, methicone coating, for example the "SI" modification, available from LCW, dimethicone coating, for example the "Covasil 3.05" modification, available from LCW, dimethicone/trimethylsiloxysilicate coating, for example the "Covasil 4.05" modification, available from LCW, lauroyllysine coating, for example the "LL" modification, available from LCW, lauroyllysine methicone coating, for example the "LL/SI" modification, available from LCW, magnesium myristate treatment, for example the "MM" modification, available from LCW, aluminum dimyristate coating, for example the "MI" modification, available from Miyoshi, perfluoropolymethyl isopropyl ether coating, for example the "FHC" modification, available from LCW, disodium stearoylglutamate coating, for example the "NAI" modification, available from Miyoshi, perfluoroalkyl phosphate treatment, for example the "PF" modification, available from Daito, acrylate/dimethicone and perfluoroalkyl phosphate coating, for example the "FSA" modification, available from Daito, polymethylhydrogensiloxane/perfluoroalkyl phosphate coating, for example the "FS01" modification, available from Daito, lauryllysine/aluminum tristearate coating, for example the "LL-StAl" modification, available from Daito, octyltriethylsilane coating, for example the "OTS" modification, available from Daito, octyltriethylsilane/perfluoroalkyl phosphate coating, for example the "FOTS" modification, available from Daito, acrylate dimethicone copolymer coating, for example the "ASC" modification, available from Daito, isopropyltitanium triisostearate coating, for example the "ITT" modification, available from Daito, microcrystalline cellulose and carboxymethylcellulose coating, for example the "AC" modification, available from Daito, acrylate copolymer coating, for example the "APD" modification, available from Daito, perfluoroalkyl phosphate/isopropyltitanium triiso-stearate coating, for example the "PF+ITT" modification, available from Daito.

Via the surface modification it is possible to establish and/or modify, for example, hydrophobicity of the pigment surface. In O/W, W/O, and W/Si emulsion systems, hydrophobic surface covering may bring about improved ease of incorporation and a longer emulsion stability.

In a further embodiment, the present invention encompasses a cosmetic formulation comprising silver-colored pigments based on nonmetallic platelet-shaped synthetic substrates coated with a titanium dioxide layer and with an ilmenite-containing layer, in which the amount of iron compounds, calculated as elemental iron, in the pigment, based on the total weight of the pigments, is less than 5% by weight, and which as a function of the coating have an iron/titanium weight ratio in accordance with $$\frac{\text{Iron content (\% by weight)}}{\text{Titanium content (\% by weight)}} \quad \text{(I)}$$

Fraction of the coating (% by weight)

from a range from 1 to 8.

In a further embodiment, the invention encompasses a cosmetic formulation comprising silver-colored pigments based on synthetic mica platelets which, after coating with a water-soluble tin compound, a water-soluble titanium compound, and in situ a water-soluble iron compound, are obtained after calcining under reducing conditions, the pigments being characterized by their color-neutral silver hue and low chroma values with a measurement geometry of 110°, relative to the angle of emergence of the light irradiated at 45°, of $C^*_{110} \leq 2.4$, measured on the basis of coatings applied to metal panels.

In a further embodiment, the invention encompasses a cosmetic formulation comprising silver-colored pigments based on synthetic mica platelets having a lightness L* of more than 90, preferably more than 92, more preferably more than 95, which, after application and drying, give a coating system an unusual strong glitter effect.

In another embodiment, the invention encompasses a cosmetic formulation comprising silver-colored pigments which in terms of their visual appearance are indistinguishable or not substantially distinguishable from metallic effect pigments, and whose flop index, as a function of the average particle size $D_{50}$, is virtually identical with that of aluminum effect pigments.

In one preferred embodiment, the ilmenite-containing layer of the silver-colored pigments is located on the outside in the layer construction and is optionally surrounded with at least one protective layer. In a particularly preferred embodiment, the silver-colored pigments comprise a single layer of titanium dioxide in the rutile modification, a single ilmenite-containing layer, optionally at least one protective layer, with at least partial penetration between the titanium dioxide layer and the ilmenite-containing layer, and with a concentration gradient between the two layers.

In cosmetic formulations, the silver-colored pigments can be combined with raw materials, auxiliaries and active ingredients that are suitable for the particular application. The concentration of the silver-colored pigments in the formulation may be between 0.001% by weight for rinse-off products and 40.0% by weight for leave-on products, based in each case on the total weight of the formulation.

The silver-colored pigments are suitable more particularly for use in cosmetics, such as, for example, body powder, face powder, compact and loose powder, powder cream, eye makeup such as eye shadow, mascara, eyeliner, liquid eyeliner, eyebrow pencil, lip care stick, lipstick, lip gloss, lip liner, hair styling compositions such as hairspray, hair mousse, hair gel, hair wax, hair mascara, permanent or semi-permanent hair colors, temporary hair colors, skincare compositions such as lotions, gels, and emulsions, and also nail varnish compositions.

The silver-colored pigments can also be used advantageously in blends with transparent and opaque white, chromatic, and black pigments, and also with further effect pigments, in the cosmetic formulation of the invention.

In order to obtain specific color effects it is possible in the cosmetic applications, in addition to the silver-colored pigments, to use other colorants and/or conventional effect pigments and/or mixtures thereof in variable proportions. Conventional effect pigments that can be used include, for example, commercial pearlescent pigments based on natural mica platelets coated with high-index metal oxides (e.g., the Prestige product group from Sudarshan Chemical Industries Limited, India), BiOCl platelets, $TiO_2$ platelets, pearlescent pigments based on synthetic mica platelets coated with high-index metal oxides (e.g., the SynCrystal product group from Eckart) or based on glass platelets coated with high-index metal oxides (e.g., the MIRAGE product group from Eckart), based on $Al_2O_3$ or $SiO_2$ platelets coated with high-index metal oxides, or based on BiOCl or $TiO_2$ platelets coated with high-index and/or low-index metal oxides. A further possibility is to add metallic effect pigments, such as the Visionaire product group from Eckart, for example. The colorants may be selected from inorganic or organic pigments.

Besides the silver-colored pigment and, where appropriate, further coloring and/or effect-imparting components, the cosmetic formulation of the invention may comprise at least one micronized wax. The micronized wax may influence the haptic properties of the cosmetic formulation of the invention. Where the cosmetic formulation of the invention is, for example, a nail varnish, then the addition of at least one micronized wax may influence both its optical properties and its haptic properties. The optical and haptic effect to be achieved is dependent here on, among other things, the particle size of the at least one micronized wax.

Micronized waxes are usually solid at room temperature (25° C.) and convert from the solid state to the liquid state above their melting range without decomposition. The consistency of the micronized waxes can range from solid to brittly hard. Micronized waxes can be translucent to opaque, and they can also be additionally colored with a cosmetically approved colorant. The micronized waxes can start to melt at a temperature as low as 40° C. Preferably, the melting range is between 51 and 399° C., further preferably between 71 and 389° C., more preferably between 91 and 379° C. and especially preferably between 111 and 369° C. The melting range of the micronized waxes is determined here in accordance with the DGF (Deutsche Gesellschaft für Fettwissenschaften—German Society for Fat Sciences) standard method C-IV 3a using a melting point measuring device (model 5A 6797, Gallenkamp).

Micronized waxes which can be used are natural and/or synthetic waxes. Furthermore, micronized waxes which can be used are preferably natural and/or synthetic waxes colored using cosmetically approved colorants. Moreover, mixtures of in each case differently colored and/or uncolored micronized waxes can also be added to the cosmetic formulation of the invention.

Natural micronized waxes which can be used are, for example, micronized beeswax (INCI: Cera Alba Beeswax), micronized candelilla wax (INCI: Candellila Cera) or micronized carnauba wax (INCI: Copernicia Cerifera (Carnauba) Wax), commercially available e.g. as Carnauba Super-Micropowder (Kahl) or Microcare 350 (Micro Powders). It is of course also possible to add different natural micronized waxes to the cosmetic formulation of the invention.

Mixtures of natural and synthetic micronized waxes can likewise be used. These include, inter alia, micronized carnauba/PE wax (INCI: Carnauba/Polyethylene), commercially available as e.g. Microcare 300, Microcare 310 (Micro Powders) or micronized carnauba/synthetic wax (INCI: Carnauba/Synthetic Wax), commercially available as e.g. Microcare 325 (Micro Powders).

Biodegradable biopolymers in micronized form such as e.g. polylactic acid (INCI: Polylactic Acid), commercially available e.g. as Ecosoft 608, Ecosoft 608X (Micro Powders) and Ecosoft 611 (INCI: Polylactic Acid Copernecia Cerifera (Carnauba) Wax, Micro Powders) can also be used in the cosmetic formulation of the invention.

Micronized waxes which can be used are, inter alia, synthetic waxes (INCI: (Oxidized) Synthetic Wax), commercially available e.g. as Microease 110×F, Microease 1105, Microease 114 S, Microease 116 (Micro Powders), micronized PE waxes, commercially available e.g. as Ceraflour 990 or Ceraflour 991 (BYK-Chemie), as Ceridust VP 3610 or TP Ceridust 6050 M (Clariant), as PE Super Micropowder (INCI: Polyethylene, Kahl), as Micropoly 200, Micropoly 210, Micropoly 220, Micropoly 220L, Micropoly 250S (INCI: (Oxidized) Polyethylene, Micro Powders) or as PE Microspheres (Cospheric), micronized PP waxes, commercially available as Ceraflour 913, Ceraflour 914, Ceraflour 915, Ceraflour 916 (BYK-Chemie), Synafil W 1234 (INCI: Polypropylene, Eckart) or as Mattewax 511 (INCI: Polypropylene, Micro Powders), micronized PMMA waxes (Polymethyl methacrylate, CAS: 9011-14-7), commercially available e.g. as PMMA Microspheres (Cospheric) or micronized polytetrafluoroethylene waxes (INCI: PTFE), commercially available as e.g. PTFE-Super Micropowder (Kahl), Microslip 519, Microslip 519 L (Micro Powders) or Ceridust 9202 F, Ceridust 9205 F (Clariant).

It is also possible to use mixtures of different micronized synthetic waxes such as, for example, of PE/polytetrafluoroethylene (INCI: Polyethylene/PTFE), commercially available e.g. as PE-PTFE Super Micropowder (Kahl), Microsilk 419 (Micro Powders) or Ceridust 3920 F or Ceridust 9325 F (Clariant), of PE/polytetrafluoroethylene/synthetic wax (INCI: Polyethylene/PTFE/Synthetic Wax), commercially available e.g. as Microsilk 418 (Micro Powders), of PP/polytetrafluoroethylene (INCI: Polypropylene/PTFE), commercially available inter alia as Microsilk 920 (Micro Powders) or of polyethylene/organic ester, such as Ceridust 3831 (Clariant).

A micronized bistearylethylenediamide wax, commercially available as Ceridust 3910 (Clariant), can likewise be used.

Synthetic micronized waxes colored with colorants can also be added to the cosmetic formulation of the invention. Mention is to be made here inter alia of the colored microspheres, such as white, black, blue, green, orange, pink, purple, red, yellow or gray microspheres (Cospheric). Alternatively or additionally, substrates, e.g. hollow glass beads, coated with titanium dioxide, as known from US 2011/0052804 A1, can be used.

The micronized waxes can optionally also be added in the form of a dispersion to the cosmetic formulation of the invention. Examples of commercially available dispersions (Micro Powders) are Microspersion 220PC (INCI: Polyethylene, Isohexadecane), Microspersion 419PC (INCI: Polyethylene, PTFE, Isohexadecane), Microspersion 511PC (INCI: Polypropylene, Isodecane, Polyethylene) or Microspersion 519PC (INCI: PTFE, Isodecane, Polyethylene).

Preferably, uncolored synthetic micronized waxes are added to the cosmetic formulation of the invention.

In a further embodiment, mixtures which comprise at least one micronized wax and at least one type of hollow glass beads can also be added to the cosmetic formulation of the invention. Hollow glass beads which can be used are, for example, Hollow Glass Microspheres (sodium silicate CAS No. 1344-09-8, sodium borate CAS No. 7775-19-1, amorphous silicon dioxide CAS No. 7631-86-9; Cospheric). The average particle size $D_{50}$ of the hollow glass beads is in a range from 27 to 90 µm, preferably in a range from 45 to 75 µm and more preferably in a range from 53 to 63 µm. According to one preferred embodiment, the fraction of micronized wax, based on the total weight of micronized wax and hollow glass beads, is more than 50% by weight, more preferably more than 65% by weight.

In a further embodiment, a mixture of colored and uncolored micronized waxes of identical or different particle size and/or of identical or different chemical composition of the wax matrix can be added to the cosmetic formulation of the invention.

In a further embodiment, the cosmetic formulation of the invention comprises the nonmetallic platelet-shaped synthetic substrates without further coating and/or the nonmetallic platelet-shaped synthetic substrates which have been provided with a surface modification. Where the nonmetallic platelet-shaped synthetic substrates are synthetic mica platelets, they are available commercially, for example, in the form of Synafil S 1050 or Synafil S 525 (both from Eckart).

EXAMPLES

The examples which follow are intended to elucidate the invention in more detail, though without restricting it. All percentages are to be understood as % by weight.

I Examples of Inventive Cosmetic Formulations

Example 1

Water-in-Silicone Body Lotion

| INCI name | Product name | % by weight | Manufacturer/Supplier |
|---|---|---|---|
| Phase A | | | |
| Cyclopentasiloxane (and) Dimethiconol | Dow Corning 1501 | 11.20 | Dow Corning |
| Cyclopentasiloxane | Xiameter PMX-0245 Cyclosiloxane | 5.75 | Dow Corning |
| Cyclopentasiloxane (and) PEG/PPG- 18/18 Dimethicone | Dow Corning 5225 C | 13.80 | Dow Corning |
| C 30-45 Alkyl Methicone | Dow Corning Cosmetic Wax AMS-C30 | 3.45 | Dow Corning |
| | Pigment from example 21 | 1.00 | |
| Phase B | | | |
| Polysorbate 20 | Tween 20 | 0.60 | Croda |
| Phenoxyethanol (and) Methylparaben (and) Ethylparaben (and) Butylparaben (and) Propylparaben (and) Isobutylparaben | Uniphen P-23 | 0.35 | Induchem |
| Sodium Chloride | Sodium Chloride | 0.75 | VWR |
| Aqua | Water | 63.10 | |

The pigment from example 21 can be used in a range from 0.2% to 2.5% by weight, based on the total weight of the body lotion formulation. The formulation can be balanced out to 100% by weight using water.

Phase A was mixed and heated to 75° C., phase B, after mixing, was heated to 70° C., and then phase B was added slowly, with homogenization, to phase A. The emulsion was cooled with stirring and was dispensed into an appropriate container.

Example 2

Eye Shadow Cream

| INCI name | Product name | % by weight | Manufacturer/Supplier |
|---|---|---|---|
| Phase A | | | |
| Castor Oil | Castor Oil | 43.70 | Honeywell Riedel-de Haen |

-continued

| INCI name | Product name | % by weight | Manufacturer/Supplier |
|---|---|---|---|
| Ethylhexyl Palmitate | Cegesoft C24 | 6.00 | Cognis |
| Cocos Nucifera (Coconut) Oil | Lipovol C-76 | 7.00 | Lipo Chemicals |
| Cera Alba | Ewacera 12 | 6.00 | H. Erhard Wagner |
| Isopropyl Lanolate | Ewalan IP | 5.00 | H. Erhard Wagner |
| Persea Gratissima (Avocado) Oil and Hydrogenated Vegetable Oil | Avocado Butter | 7.00 | Impag |
| Magnesium Stearate | Magnesium Stearate | 3.00 | Sigma-Aldrich |
| Bis-Hydroxyethoxypropyl Dimethicone | Dow Corning 5562 Carbinol Fluid | 7.00 | Dow Corning |
| Dimethicone/Vinyl Dimethicone Crosspolymer and Silica | Dow Corning 9701 Cosmetic Powder | 5.00 | Dow Corning |
| Phenoxyethanol (and) Methylparaben (and) Ethylparaben (and) Butylparaben (and) Propylparaben (and) Isobutylparaben | Uniphen P-23 | 0.30 | Induchem |
| Phase B | | | |
| | Pigment from example 20 | 10.00 | |

The pigment from example 20 can be used in a range from 5% to 22.0% by weight, based on the total weight of the eye shadow formulation. The formulation can be balanced out to 100% by weight using Castor Oil.

Phase A was mixed and heated to 85° C., and phase B was then added with stirring to phase A. The mixture is dispensed into an appropriate container and then cooled to room temperature.

Example 3

Shower Gel

| INCI name | Product name | % by weight | Manufacturer/Supplier |
|---|---|---|---|
| Phase A | | | |
| | Pigment from example 21 | 0.50 | |
| Aqua | Water | 58.10 | |
| Acrylates Copolymer | Carbopol Aqua SF-1 | 5.50 | Lubrizol |
| Phase B | | | |
| Sodium Hydroxide | NaOH (10% by weight) | 1.50 | |
| Phase C | | | |
| Sodium Laureth Sulfate | Texapon NSO | 22.00 | Cognis |
| Cocamidopropyl Betaine | Tego Betain F 50 | 6.00 | Evonik |
| PEG-7 Glyceryl Cocoate | Emanon HE | 2.00 | Kao Corp. |
| Disodium Laureth Sulfosuccinate | Sectacin 103 | 2.00 | Zschimmmer & Schwarz |

-continued

| INCI name | Product name | % by weight | Manufacturer/Supplier |
|---|---|---|---|
| Phase D | | | |
| Phenoxyethanol (and) Piroctone Olamine | Nipaguard PO 5 | 0.60 | Clariant |
| Fragrance | Water Lily OA | 0.20 | Bell Flavors and Fragrances |
| Sodium Chloride | Sodium Chloride | 1.60 | VWR |

The pigment from example 21 can be used in a range from 0.01% to 1.0% by weight, based on the total weight of the shower gel formulation. The formulation can be balanced out to 100% by weight using water.

Phase A was mixed and stirred. Then phase B was added and the mixture was stirred until it had a homogeneous appearance. Phase C was weighed out separately, mixed and added to phase AB. Stirring was then repeated and phase D was added individually.

Example 4

Pressed Ave Shadow

| INCI name | Product name | % by weight | Manufacturer/Supplier |
|---|---|---|---|
| Phase A | | | |
| Mica | Silk Mica | 17.00 | VWR |
| Boron Nitride | Softouch CCS 102 | 2.50 | Momentive |
| Zinc Stearate | Zinc Stearate | 7.00 | VWR |
| Talc | Talc Powder | 43.50 | Sigma-Aldrich |
| | Pigment from example 22 | 20.00 | |
| Phase B | | | |
| Dimethicone | Xiameter PMX-200 Silicone Fluid 5cs | 5.00 | Dow Corning |
| Cyclopentasiloxane (and) Dimethicone Crosspolymer | Dow Corning 9040 Elastomer | 5.00 | Dow Corning |

The pigment from example 22 can be used in a range from 5.0% to 40.0% by weight, based on the total weight of the eye shadow formulation. The formulation can be balanced out to 100% by weight using talc.

Phase A was mixed in a high-speed mixer at 2500 rpm for 30 seconds. Then phase B was added and the mixture was mixed in the same mixer at 3000 rpm for 60 seconds. Lastly the powder mixture is shaped using an eye shadow press at 150 bar for 30 seconds.

Example 5

Hair Mascara

| INCI name | Product name | % by weight | Manufacturer/Supplier |
|---|---|---|---|
| Phase A | | | |
| Polyquaternium-16 | Luviquat FC 905 (Luviquat Exellence) | 2.70 | BASF |

-continued

| INCI name | Product name | % by weight | Manufacturer/Supplier |
|---|---|---|---|
| Propylene Glycol | 1,2-Propanediol | 1.80 | VWR |
| Methylparaben | Methyl 4-hydroxybenzoate | 0.20 | Sigma-Aldrich |
| Aqua | Water | 64.45 | |
| Phase B | | | |
| Cetearyl Alcohol | Lanette O | 5.00 | Cognis |
| Dimethicone | Xiameter PMX-200 Silicone Fluid 350cs | 1.00 | Dow Corning |
| Ceteareth-25 | Cremophor A 25 | 2.00 | BASF |
| Propylparaben | Propyl 4-hydroxybenzoate | 0.10 | Sigma-Aldrich |
| Phase C | | | |
| Hydroxypropyl-cellulose | Klucel G | 0.50 | Ashland |
| Magnesium Aluminum Silicate | Veegum HV | 0.50 | R. T. Vanderbilt |
| Aqua | Water | 19.00 | |
| Phase D | | | |
| | Pigment from example 21 | 2.50 | |
| Phenoxyethanol (and) Methylparaben (and) Butylparaben (and) Ethylparaben (and) Propylparaben (and) Isobutylparaben | Phenonip | 0.20 | Clariant |
| Fragrance | Blue Shadow ÖKO | 0.05 | Bell Flavors and Fragrances |

The pigment from example 21 can be used in a range from 1.0% to 10.0% by weight, based on the total weight of the hair mascara formulation. The formulation can be balanced out to 100% by weight using the water from phase A.

Phase A and phase B were heated separately to 80° C., and then phase B was added slowly to phase A. In a separate vessel, Klucel and Veegum were added to the water of phase C. Then phase AB was cooled to 40° C. and, in the course of cooling, phases C and D were added with stirring.

Example 6

Hair Gel

| INCI name | Product name | % by weight | Manufacturer/Supplier |
|---|---|---|---|
| Phase A | | | |
| | Pigment from example 21 | 0.10 | |
| Ammonium Acryloyldimethyltaurate/VP Copolymer | Aristoflex AVC | 1.40 | Clariant |
| Citric Acid | Citric Acid | 0.10 | VWR |
| Aqua | Water | 55.10 | |
| Phase B | | | |
| PVP | Luviskol K 30 Powder | 1.50 | BASF |
| Propylene Glycol, Diazolidinyl Urea, Methylparaben, Propylparaben | Germaben II | 0.20 | International Specialty Products |
| Triethanolamine | Triethanolamine | 1.20 | VWR |
| Water | Aqua | 40.40 | |

The pigment from example 21 can be used in a range from 0.01% to 2.0% by weight, based on the total weight of the hair gel formulation. The formulation can be balanced out to 100% by weight using water.

The pigment from example 21 was stirred together with water from phase A, Aristoflex AVC and Citric Acid were added with stirring, and the mixture was mixed at a speed of 800 rpm for 15 minutes. Phase B was dissolved until it formed a homogeneous solution, after which phase B was added to phase A and the phases were mixed.

Example 7

Body Powder

| INCI name | Product name | % by weight | Manufacturer/Supplier |
|---|---|---|---|
| Phase A | | | |
| Mica | Silk Mica | 58.70 | VWR |
| Talc | Talc Powder | 18.00 | Sigma-Aldrich |
| Boron Nitride | Softouch CCS 102 | 5.00 | Advanced Ceramics |
| Nylon-12 | Orgasol 2002 D/Nat | 8.00 | Arkema |
| Magnesium Stearate | Magnesium Stearate | 6.00 | Sigma-Aldrich |
| Methylparaben, Propylparaben | Rokonsal SSH-1 | 0.30 | ISP Biochema |
| | Pigment from example 20 | 2.00 | |
| Phase B | | | |
| Tridecyl Stearate (and) Tridecyl Trimellitate (and) Dipentaerythrityl Hexacaprylate/Hexacaprate | Lipovol MOS-130 | 2.00 | Lipo Chemicals |

The pigment from example 20 can be used in a range from 0.2% to 5.0% by weight, based on the total weight of the body powder formulation. The formulation can be balanced out to 100% by weight using Silk Mica.

Phase A was mixed, then phase B was added to phase A and the body powder was dispensed into a suitable vessel.

Example 8

Lip Gloss

| INCI name | Product name | % by weight | Manufacturer/Supplier |
|---|---|---|---|
| Phase A | | | |
| Hydrogenated Polyisobutene (and) Ethylene/Propylene/Styrene Copolymer (and) Butylene/Ethylene/Styrene Copolymer | Versagel ME 750 | 79.00 | Calumet Penreco |
| Simmondsia Chinensis (Jojoba) Seed Oil | Jojoba Oil-Natural/Golden | 2.00 | BioChemica |
| Caprylyl Trimethicone | Silcare Silicone 31M50 | 7.00 | Clariant |
| Stearyl Dimethicone | Silcare Silicone 41M65 | 3.20 | Clariant |

-continued

| INCI name | Product name | % by weight | Manufacturer/Supplier |
|---|---|---|---|
| Hydrogenated Polydecene | Nexbase 2002 | 4.00 | Jan Dekker |
| Isopropyl Myristate | Isopropyl Myristate | 4.50 | VWR |
| Phase B | | | |
| | Pigment from example 21 | 0.10 | |
| Propylparaben | Propyl 4-hydroxybenzoate | 0.20 | Sigma-Aldrich |

The pigment from example 21 can be used in a range from 0.10% to 8.00% by weight, based on the total weight of the lip gloss formulation. The formulation can be balanced out to 100% by weight using Versagel ME 750.

Phase A was heated to 85° C., and then the ingredients of phase B were added individually to phase A, and the composition was stirred until its consistency was uniform, after which it was dispensed into a lip gloss vessel.

Example 9

Lip Contour Pencil

| INCI name | Product name | % by weight | Manufacturer/Supplier |
|---|---|---|---|
| Phase A | | | |
| Hydrogenated Coco-Glycerides | Softisan 100 | 12.35 | Sasol Wax |
| Candelilla Cera | Ewacera 42 | 14.00 | H. Erhard Wagner |
| Magnesium Stearate | Magnesium Stearate | 6.00 | Sigma-Aldrich |
| Stearic Acid | Kortacid 1895 | 8.50 | Akzo Nobel |
| Hydrogenated Coconut Oil | Lipex 401 | 8.00 | Aarhus Karlshamn |
| Cetyl Palmitate | Kahlwax 7157 | 7.00 | Kahl |
| Caprylic/Capric Triglyceride | Liponate GC-K | 3.60 | Lipo Chemicals |
| Soybean Glycerides (and) *Butyrospermum Parkii* | Lipex L'sens | 15.00 | Aarhus Karlshamn |
| Tocopheryl Acetate | dl-alpha-Tocopheryl Acetate | 0.25 | Jan Dekker |
| Methylparaben; Propylparaben | Rokonsal SSH-1 | 0.30 | ISP Biochema |
| Phase B | | | |
| | Pigment from example 22 | 25.00 | |

The pigment from example 22 can be used in a range from 15% to 25% by weight, based on the total weight of the lip contour pencil formulation. Alternatively, in addition to the pigment from example 6, it is possible to add further color pigments and/or effect pigments, although the maximum level of pigmentation of 25% by weight pigment ought not to be exceeded.

Phase A was heated to 85° C. and then phase B was added to phase A with stirring until the composition was uniform. Thereafter the mixture was introduced while hot into a pencil mold.

Example 10

Lipstick

| INCI name | Product name | % by weight | Manufacturer/Supplier |
|---|---|---|---|
| Phase A | | | |
| Carnauba Wax | Ewacera 34 | 4.50 | H. Erhard Wagner |
| Cera Alba | Ewacera 12 | 3.50 | H. Erhard Wagner |
| Candelilla Cera Extract | Ewacera 42 | 4.00 | H. Erhard Wagner |
| Microcrystalline Wax | TeCero-Wax 1030 K | 7.20 | TH. C. Tromm |
| Cetyl Palmitate | Kahlwax 7157 | 2.00 | Kahl |
| Hydrogenated Coco-Glycerides | Softisan 100 | 5.00 | Sasol Wax |
| Petrolatum | Penreco Blond | 5.80 | Calumet Penreco |
| Cetearyl Ethylhexanoate | Luvitol EHO | 10.70 | BASF |
| Tocopheryl Acetate | dl-alpha-Tocopheryl Acetate | 0.50 | Jan Dekker |
| Castor Oil | Castor Oil | 46.60 | Honeywell Riedel-de Haen |
| Phase B | | | |
| | Pigment from example 20 | 10.00 | |
| Methylparaben, Propylparaben | Rokonsal SSH-1 | 0.20 | ISP Biochema |

The pigment from example 20 can be used in a range from 0.5% to 21.0% by weight, based on the total weight of the lipstick formulation. The formulation can be balanced out to 100% by weight using castor oil.

Phase A was heated to 85 C, and then phase B was added to phase A and the phases were mixed. This mixture was subsequently dispensed at a temperature of 75° C. in a lipstick mold.

Example 11

Liquid Eye Liner

| INCI name | Product name | % by weight | Manufacturer/Supplier |
|---|---|---|---|
| Phase A | | | |
| Aqua | Water | 66.70 | |
| Water/carbon black dispersion | MBD 201 | 3.00 | Geotech |
| Acrylates Copolymer | Covacryl E14 | 10.00 | LCW |
| Magnesium Aluminum Silicate | Veegum HV | 1.00 | C. H. Erbslöh |
| Phase B | | | |
| Propylene Glycol | 1,2-Propanediol | 3.00 | VWR |
| Triethanolamine | Triethanolamine | 1.40 | VWR |
| Phase C | | | |
| Xanthan Gum | Keltrol CG-T | 0.30 | CP Kelco |

-continued

| INCI name | Product name | % by weight | Manufacturer/Supplier |
|---|---|---|---|
| Phase D | | | |
| | Pigment from example 22 | 3.00 | |
| Mica | Silk Mica | 2.00 | VWR |
| Phase E | | | |
| Stearic Acid | Kortacid 1895 | 2.80 | Akzo Nobel |
| Glyceryl Stearate | Aldo MS K FG | 0.80 | Lonza |
| Oleyl Alcohol | HD-Ocenol 90/95 V | 0.50 | Cognis |
| Phenoxyethanol (and) Methylparaben (and) Ethylparaben (and) Butylparaben (and) Propylparaben (and) Isobutylparaben | Uniphen P-23 | 0.50 | Induchem |
| Phase F | | | |
| Dimethicone (and) Trisiloxane | Xiameter PMX-1184 Silicone Fluid | 5.00 | Dow Corning |

The pigment from example 22 can be used in a range from 0.5% to 8.0% by weight, based on the total weight of the eye liner formulation. The formulation can be balanced out to 100% by weight using water.

Veegum was dispersed in phase A and stirred for 15 minutes, after which phase B was added to phase A, and then phase C to phase AB, followed by stirring again for 10 minutes. Then phase D was added to phase ABC and the mixture was heated to 75° C., and phase E was likewise heated to 75° C. and then added to phase ABCD. After cooling to 60° C. had taken place, phase F was added, and the mixture was dispensed into a suitable vessel.

Example 12

Mousse

| INCI name | Product name | % by weight | Manufacturer/Supplier |
|---|---|---|---|
| Phase A | | | |
| Cyclopentasiloxane | Xiameter PMX-0245 Cyclosiloxane | 8.60 | Dow Corning |
| Hydrogenated Polyisobutene | MC 30 | 4.00 | Sophim |
| Dimethicone (and) Dimethicone Crosspolymer | Dow Corning 9041 Silicone Elastomer Blend | 37.14 | Dow Corning |
| Squalane | Squalane | 5.74 | Impag |
| Isononyl Isononanoate | Dermol 99 | 10.16 | Akzo International |
| Hydrogenated Jojoba Oil | Jojoba Butter LM | 2.15 | Desert Whale |
| Hydrogenated Jojoba Oil | Jojoba Butter HM | 1.00 | Desert Whale |
| C30-45 Alkyl Methicone (and) C30-45 Olefin | Dow Corning AMS-C30 Cosmetic Wax | 1.15 | Dow Corning |
| Stearyl Dimethicone | Dow Corning 2503 Cosmetic Wax | 0.47 | Dow Corning |
| Cyclopentasiloxane (and) Polypropylsilsesquioxane | Dow Corning 670 Fluid | 5.00 | Dow Corning |
| Phase B | | | |
| Dimethicone/Vinyl Dimethicone Crosspolymer | Dow Corning 9506 Powder | 16.02 | Dow Corning |
| Silica Dimethyl Silylate | Covasilic 15 | 0.17 | LCW |
| Talc | Talc Powder | 5.00 | Sigma-Aldrich |
| | Pigment from example 20 | 3.00 | |
| Phase D | | | |
| Propylene Glycol, Diazolidinyl Urea, Methylparaben, Propylparaben | Germaben II | 0.40 | International Specialty Products |

The pigment from example 20 can be used in a range from 0.1% to 8.0% by weight, based on the total weight of the mousse formulation. The formulation can be balanced out to 100% by weight using Dow Corning 9041 elastomer.

Phase A was mixed and heated until everything had melted. Phase B was weighed out separately and mixed with a high-speed mixer at 2400 rpm for 60 seconds. Half of the melted phase A was added to phase B, and mixing was repeated in the mixer at 2400 rpm for 30 seconds. Then the remainder of phase B was likewise added to phase A, followed again by mixing at 2400 rpm for 30 seconds. Lastly, phase C is added to phase AB and mixing is repeated at 2400 rpm for 30 seconds in the high-speed mixer.

Example 13

Nail Varnish

| INCI name | Product name | % by weight | Manufacturer/Supplier |
|---|---|---|---|
| Phase A | | | |
| | Pigment from example 20 | 2.00 | |
| Phase B | | | |
| Butyl acetate (and) Ethyl acetate (and) Nitrocellulose (and) Isopropyl Alcohol | International Lacquers Nailpolish & Care Base 359 | 98.00 | International Lacquers |

The pigment from example 20 can be used in a range from 0.1% to 10.0% by weight, based on the total weight of the nail varnish formulation. The formulation can be balanced out to 100% by weight using International Lacquers Nailpolish.

Phase A and phase B were mixed and then dispensed into an appropriate container.

Example 14

Nail Varnish with Soft Touch Effect

| INCI name | Product name | % by weight | Manufacturer/Supplier |
|---|---|---|---|
| Phase A | | | |
| | Pigment from example 20 | 2.00 | |
| | Ceraflour 913 | 5.00 | Byk Chemie |
| Phase B | | | |
| Butyl acetate (and) Ethyl acetate (and) Nitrocellulose (and) Isopropyl Alcohol | International Lacquers Nailpolish & Care Base 359 | 93.00 | International Lacquers |

The pigment from example 20 can be used in a range from 0.1% to 10.0% by weight, based on the total weight of the nail varnish formulation. The formulation can be balanced out to 100% by weight using International Lacquers Nailpolish.

Phase A was mixed, added to phase B, and then the nail varnish was dispensed into an appropriate container.

Example 15

Aqueous Nail Varnish

The pigments from examples 20 to 22 can be used in an aqueous nail varnish according to WO 2007/115675 A2 example 1. The level of pigmentation in this case is 0.1% to 10.0% by weight, based on the total weight of the formulation.

Example 16

Liquid Eye Shadow

| INCI name | Product name | % by weight | Manufacturer/Supplier |
|---|---|---|---|
| Phase A | | | |
| Water | Aqua | 70.10 | |
| Glycerin | Pricerine 9090 | 6.00 | Croda |
| Phase B | | | |
| PEG-800 | Polyglycol 35000 S | 0.60 | Clariant |
| Allantoin | Allantoin | 0.30 | 3V |
| Ammonium Acryloyldimethyl-taurate/VP Copolymer | Aristoflex AVC | 0.80 | Clariant |
| Acrylates Copolymer | Worlee Micromer CEK 20/50 | 5.00 | Worlee |
| Phase C | | | |
| | Pigment from example 22 | 10.00 | |
| Divinyldimethicone/ Dimethicone Copolymer C12-C13 Pareth-3, C12-C13 Pareth-23 | Dow Corning HMW 2220 Non-Ionic Emulsion | 6.00 | Dow Corning |
| Fragrance | Water Lily OA | 0.20 | Bell Flavors and Fragrances |
| Phenoxyethanol (and) Methylparaben (and) Butylparaben (and) Ethylparaben (and) Propylparaben (and) Isobutylparaben | Phenonip | 1.00 | Clariant |

The pigment from example 22 can be used in a range from 0.10% to 17.00% by weight, based on the total weight of the eye shadow formulation. The formulation can be balanced out to 100% by weight using water.

Phase A was stirred, and then the ingredients of phase B were added individually to phase A and the mixture was stirred until its consistency was uniform.

Thereafter the ingredients of phase C were added individually to phase AB and the mixture was again stirred until its consistency was uniform.

II Preparation of the Nonmetallic Platelet-Shaped Synthetic Substrates and of the Silver-Colored Pigments for Use in Cosmetic Formulations

Example 17

Preparation and Classification of Synthetic fluorophlogopite mica $KMg_3(AlSi_3O_{10})F_2$ 40 parts of anhydrous silica, 30 parts of magnesium oxide, 13 parts of aluminum oxide and 17 parts of potassium hexafluorosilicate were mixed and melted at 1500° C. On cooling to 1350° C., crystallization of fluorophlogopite $(KMg_3(AlSi_3O_{10})F_2)$ commenced. The fluorophlogopite was then comminuted and delaminated using a laboratory edge runner mill from American Cyanamid Company.

The resulting platelet-shaped fluorophlogopite was calcined in a muffle furnace at 1100° C. for an hour and then classified using a laboratory sieve.

In the course of the classification, two fractions were obtained, with the following particle size distribution (MALVERN Mastersizer MS 2000):

Fraction 1: $D_{10}=11.4$ μm, $D_{50}=21.8$ μm, $D_{90}=40.0$ μm,
Fraction 2: $D_{10}=5.6$ μm, $D_{50}=12.2$ μm, $D_{90}=24.8$ μm The composition of the synthetic mica platelets, measured by XRF, can be found in Table 3.

Example 18

Preparation of Synthetic fluorophlogopite mica $KMg_20.5(AlSi_2O_{10})F_2$ 30 parts of anhydrous silica, 25 parts of magnesium oxide, 10 parts of aluminum oxide and 15 parts of potassium hexafluorosilicate were mixed with one another and melted at 1500° C. The liquid mixture was subsequently crystallized slowly at temperatures of 1350° C. to give synthetic fluorophlogopite $(KMg_{20}0.5(AlSi_2O_{10})F_2)$. The synthetic mica lumps obtained were comminuted and subsequently delaminated using a laboratory edge runner mill from American Cyanamid Company.

The resulting platelet-shaped fluorophlogopite was subsequently calcined in a muffle furnace at 1100° C. for an hour and then classified accordingly using a laboratory sieve. In the course of the classification, two fractions were obtained, with the following particle size distribution (MALVERN Mastersizer MS 2000):

Fraction 1: $D_{10}$=10.2 µm, $D_{50}$=20.7 µm, $D_{90}$=42.2 µm,
Fraction 2: $D_{10}$=6.5 µm, $D_{50}$=13.4 µm, $D_{90}$=25.8 µm The composition of the synthetic mica platelets, measured by XRF, can be found in Table 3.

Example 19

Classification of Glass Platelets

A suspension of 200 g of glass platelets (average thickness: 1 µm, standard deviation in thickness: about 40%) in DI water (about 3% by weight, DI: fully demineralized) was classified using a 100 µm sieve, and the material passing through the sieve was sieved in turn through a 63 µm sieve. The material passing through this sieve in turn was passed through a 36 µm sieve. This sieving procedure was repeated twice with sieve residue obtained on the 36 µm sieve. In this way a glass platelet fraction was obtained that had the following particle size distribution (MALVERN Mastersizer MS 2000): $D_{10}$=17 µm, $D_{50}$=33 µm, $D_{90}$=59 µm.

Example 20

Coating of the Synthetic Mica from Example 17 with Ilmenite 270 g of the synthetic mica from example 17 (fraction 1) were suspended in 1350 ml of DI water and heated to 80° C. with turbulent stirring. The pH was lowered to 1.9 using dilute hydrochloric acid. Then an "$SnO_2$" layer was deposited on the substrate surface. This layer was formed by adding a solution of 3 g of $SnCl_4 \times 5H_2O$ (in 10 ml of conc. HCl plus 50 ml of DI water) with simultaneous metering of a 10% strength aqueous sodium hydroxide solution. Thereafter the pH was lowered to pH 1.6 using dilute hydrochloric acid, after which a solution of 400 ml of $TiCl_4$ (200 g of $TiO_2$/l of DI water) and also, at the same time, a 10% strength aqueous sodium hydroxide solution were metered into the suspension. After the end of the coating procedure, stirring was continued for 1 hour, after which the pH was adjusted to 2.9 using dilute aqueous sodium hydroxide solution. Thereafter 30 ml of $FeCl_3$ (280 g of $Fe_2O_3$/l of DI water) and also, simultaneously, a 10% strength aqueous sodium hydroxide solution were metered into the suspension, which was stirred for 1 hour and filtered, and the filter cake was washed with DI water. The filter cake was calcined in a tube furnace at 800° C. under an atmosphere of forming gas (70% of $N_2$/30% of $H_2$) for 2 hours. This gave silver-colored pigments of extremely high luster with a metallic appearance. The pigments had the following particle size distribution (MALVERN Mastersizer MS 2000): $D_{10}$=12.4 µm, $D_{50}$=23.9 µm, $D_{90}$=43.1 µm.

Example 21

Coating of the Synthetic Mica from Example 18 with Ilmenite 270 g of the synthetic mica from example 18 (fraction 2) were suspended in 2000 ml of DI water and heated to 80° C. with turbulent stirring. The pH was lowered to 1.9 using dilute hydrochloric acid. Then an "$SnO_2$" layer was deposited on the substrate surface. This layer was formed by adding a solution of 5 g of $SnCl_4 \times 5 H_2O$ (in 10 ml of conc. HCl plus 50 ml of DI water) with simultaneous metering of a 10% strength aqueous sodium hydroxide solution. Thereafter a solution of 650 ml of $TiCl_4$ (200 g of $TiO_2$/l of DI water) and also, at the same time, a 10% strength aqueous sodium hydroxide solution were metered into the suspension. After the end of the coating procedure, stirring was continued for 1 hour, after which the pH was adjusted to 2.9 using dilute aqueous sodium hydroxide solution. Thereafter 30 ml of $FeCl_3$ (280 g of $Fe_2O_3$/l of DI water) and also, simultaneously, a 10% strength aqueous sodium hydroxide solution were metered into the suspension, which was stirred for 1 hour and filtered, and the filter cake was washed with DI water. The filter cake was calcined in a tube furnace at 800° C. under an atmosphere of forming gas (70% of $N_2$/30% of $H_2$) for 2 hours.

This gave lustrous silver-colored pigments with a metallic appearance and a high opacity. The pigments had the following particle size distribution (MALVERN Mastersizer MS 2000): $D_{10}$=7.3 µm, $D_{50}$=13.3 µm, $D_{90}$=25.4 µm.

Example 22

Coating of the Glass Platelets from Example 19 with Ilmenite 200 g of glass platelets from example 19 were suspended in 1800 ml of DI water and heated with turbulent stirring to 70° C. The pH was lowered to 1.9 with dilute hydrochloric acid. Then an "$SnO_2$" layer was deposited on the substrate surface. This layer was formed by adding a solution of 5 g of $SnCl_4 \times 5 H_2O$ (in 15 ml of conc. HCl plus 65 ml of DI water) with simultaneous metered addition of a 10% strength aqueous sodium hydroxide solution. This was followed by stirring for 10 minutes, after which a solution of 100 ml of $TiCl_4$ (200 g of $TiO_2$/l of DI water) was metered into the suspension in parallel with 10% strength aqueous sodium hydroxide solution. After the end of the coating procedure, stirring was continued for an hour, after which the pH was adjusted to 2.9 with dilute aqueous sodium hydroxide solution. Thereafter 10 ml of $FeCl_3$ (280 g of $Fe_2O_3$/l of DI water) were metered into the suspension in parallel with 10% strength aqueous sodium hydroxide solution, followed by stirring for an hour and filtration, and the filter cake was washed with DI water. The filter cake was calcined in a tube furnace at 550° C. under an atmosphere of forming gas (70% of $N_2$/30% of $H_2$) for 2 hours.

This gave strongly glittery, silver-colored pigments with a metallic appearance and an extremely high luster. The pigments had the following particle size distribution (MALVERN Mastersizer MS 2000):

$D_{10}$=18.4 µm, $D_{50}$=34.3 µm, $D_{90}$=61.4 µm.

Comparative Example 1

Coating of natural muscovite mica with a MALVERN Mastersizer MS 2000 particle size distribution of =11.0 µm, $D_{50}$=23.1 µm, $D_{90}$=44.4 µm with ilmenite Coating took place in exactly the way described in example 7 from WO 2004/099319 A2.

This gave silver-colored, opaque pearlescent pigments with a low luster and a low flop index. The pigments had the following particle size distribution (MALVERN Mastersizer MS 2000): $D_{10}$=11.6 µm, $D_{50}$=24.2 µm, $D_{90}$=46.7 µm.

Comparative Example 2

Aluminum effect pigment Stapa Metallux 2154 from Eckart. The pigments have the following particle size distribution (Cilas 1064): $D_{10}$=12.4 µm, $D_{50}$=19.8 µm, $D_{90}$=30.0 µm.

Comparative Example 3

Ilmenite-coated pearlescent pigment Iriodin 9602 WR from Merck. The pigments have the following particle size distribution (MALVERN Mastersizer MS 2000):
$D_{10}=10.1$ µm, $D_{50}=21.3$ µm, $D_{90}=40.8$ µm.

Comparative Example 4

Ilmenite-coated pearlescent pigment Iriodin 9612 WR from Merck. The pigments have the following particle size distribution (MALVERN Mastersizer MS 2000):
$D_{10}=3.0$ µm, $D_{50}=6.4$ µm, $D_{90}=12.4$ µm.

Comparative Example 5

Silvery pearlescent pigment Phoenix CFE 1001 from Eckart. The pigments have the following particle size distribution (MALVERN Mastersizer MS 2000):
$D_{10}=9.6$ µm, $D_{50}=20.3$ µm, $D_{90}=38.3$ µm.

Comparative Example 6

Coating of natural muscovite mica with a MALVERN Mastersizer MS 2000 particle size distribution of $D_{10}=11.0$ µm, $D_{50}=23.1$ µm, $D_{90}=44.4$ µm with ilmenite Coating took place in exactly the way described in example 1 from WO 2004/099319 A2.

This gave silver-colored, violet-tinged pearlescent pigments with a low luster and a low flop index. The pigments have the following particle size distribution (MALVERN Mastersizer MS 2000): $D_{10}=11.4$ µm, $D_{50}=23.8$ µm, $D_{90}=45.7$ µm.

Comparative Example 7

Identical to multilayer pearlescent pigment from example 10 of DE 10 2009 037 935 A1; average particle size (MALVERN Mastersizer MS 2000): $D_{50}=29.2$ µm.

Comparative Example 8

Identical to pearlescent pigment from example 1a of DE 10 2009 049 413 A1; average particle size (MALVERN Mastersizer MS 2000): $D_{50}=3.2$ µm.

III Characterization of the Nonmetallic Platelet-Shaped Synthetic Substrates and of the Silver-Colored Pigments Characterization took place as described below on the basis of the silver-colored pigment.

IIIa Particle Size Measurement

The size distribution curve of the nonmetallic platelet-shaped synthetic substrates and of the pigments was determined using an instrument from Malvern (instrument: MALVERN Mastersizer 2000) in accordance with manufacturer instructions. For this purpose, about 0.1 g of the substrate or pigment in question, in the form of an aqueous suspension without dispersing assistants added, was introduced using a Pasteur pipette, and with continuous stirring, into the sample preparation cell of the instrument, and subjected to measurement a number of times. The resultant averages were formed from the individual measurement results. The scattered-light signals were evaluated here in accordance with the Fraunhofer method.

The size distribution curve of the metallic effect pigment (in paste form) from comparative example 2 was measured using an instrument from Quantachrome (instrument: Cilas 1064) in accordance with manufacturer instructions. For this purpose about 1.5 g of the pigment were suspended in isopropanol, treated in an ultrasound bath (instrument: Sonorex IK 52 from Bandelin) for 300 seconds, and then introduced using a Pasteur pipette into the sample preparation cell of the instrument and subjected to measurement a number of times. The resultant averages were formed from the individual measurement results. The scattered-light signals were evaluated here in accordance with the Fraunhofer method.

The average size $D_{50}$ in the context of this invention refers to the $D_{50}$ value of the cumulative frequency distribution of the volume-averaged size distribution function as obtained by laser diffraction methods. The $D_{50}$ value indicates that 50% of the nonmetallic platelet-shaped synthetic substrates or pigments have a diameter which is the same as or less than the specified value, 20 µm for example. Correspondingly, the $D_{90}$ value indicates that 90% of the substrates or pigments have a diameter which is the same as or less than the respective value. Furthermore, the $D_{10}$ value indicates that 10% of the substrates or pigments have a diameter which is the same as or less than the respective value.

IIIb Determination of the Average Thickness of the Nonmetallic Platelet-Shaped Synthetic Substrates For the determination of the average thickness of the nonmetallic platelet-shaped synthetic substrates, the substrates or pigments were incorporated at 10% by weight into an Autoclear Plus HS two-component clear-coat varnish from Sikkens, using a sleeved brush, and, using a wire-wound doctor blade, were applied to a film (26 µm wet-film thickness) and dried. After drying for 24 hours, polished sections were prepared from these doctor-blade drawdowns and were subjected to measurement by scanning electron microscopy. In this procedure, at least 100 pigment particles were measured in order to obtain meaningful statistics. The average thickness of the synthetic mica platelets used as substrate can be seen from Table 2.

TABLE 2

| | Example 17 Fraction 1 Average thickness [nm] | Example 17 Fraction 2 Average thickness [nm] | Example 18 Fraction 1 Average thickness [nm] | Example 18 Fraction 2 Average thickness [nm] |
|---|---|---|---|---|
| $D_{10}$ | 289 | 154 | 321 | 138 |
| $D_{50}$ | 434 | 219 | 443 | 209 |
| $D_{90}$ | 734 | 318 | 779 | 294 |

The indication $D_{10}$ here means that 10% of the nonmetallic platelet-shaped synthetic substrates have an average thickness which is equal to or smaller than the stated value. Correspondingly, the $D_{50}$ or $D_{90}$ value here indicates that 50% or 90%, respectively, of the nonmetallic platelet-shaped synthetic substrates have an average thickness which is the same as or smaller than the specified value.

IIIc Determination of the Metal Oxide Content

The metal oxide contents of the nonmetallic platelet-shaped synthetic substrates or pigments were determined by means of X-ray fluorescence (XRF) analysis.

For this purpose the substrate or pigment was incorporated into a lithium tetraborate glass tablet, fixed in solid sample measuring beakers and measured therefrom. The instrument used was the Advantix ARL from Thermo Scientific.

TABLE 3

Metal oxide contents by XRF of the synthetic mica platelets used as substrate

| Metal oxide | Example 17 (% by weight) | Example 18 (% by weight) |
|---|---|---|
| $TiO_2$ | <0.1 | <0.1 |
| $SnO_2$ | <0.1 | <0.1 |
| $SiO_2$ | 42.1 | 20.3 |
| $Al_2O_3$ | 12.2 | 8.1 |
| $K_2O$ | 11.0 | 15.9 |
| $Fe_2O_3$ | 0.1 | 0.1 |
| $Cr_2O_3$ | <0.1 | <0.1 |
| $CeO_2$ | <0.1 | <0.1 |
| CaO | 0.1 | 0.1 |
| MgO | 31.6 | 27.6 |
| $Na_2O$ | 0.2 | 0.4 |
| $P_2O_5$ | <0.1 | <0.1 |
| MnO | <0.1 | <0.1 |

The % by weight figures reported in Table 3 relate in each case to the total weight of the nonmetallic platelet-shaped substrate.

TABLE 4

Magnesium oxide content of the pigments by XRF

| | MgO (% by weight) |
|---|---|
| Example 20 | 19.6 |
| Example 21 | 17.1 |
| Comparative example 1 | 0.3 |
| Comparative example 3 | 0.3 |
| Comparative example 4 | 0.2 |
| Comparative example 5 | 0.3 |

The % by weight figures reported in Table 4 relate in each case to the total weight of the respective pigment.

The weight fractions reported in Table 5 relate in each case to the total weight of the pigment.

The iron values reported in Table 5 are values converted arithmetically to elemental iron. For this purpose, the contents data for the iron compounds detectable in the pigment by XRF were converted arithmetically to elemental iron. For the calculation of the Fe/Ti weight ratio reported in Table 5, the titanium oxide content of the pigment as measured by means of XRF was converted arithmetically to elemental titanium.

For the Fe/Ti weight ratio (layer) reported in Table 5, account was taken of the fraction of the coating on the pigments, in accordance with $$\frac{\text{Iron content (\% by weight)}}{\text{Titanium content (\% by weight)}} \text{Fraction of the coating (\% by weight)}.$$

The fraction of the coating (% by weight) is defined by the total weight of the pigment (100% by weight) minus the fraction of the substrate (% by weight).

IIId Determination of the Lead Contents Via Solids AAS

The lead contents of the synthetic mica platelets and of the pigments based on synthetic mica platelets were determined using solids graphite tube atomic absorption spectrometry. The instrument used was a ZEENIT 650 with SSA 600 solids sampler (manufacturer: Analytik Jena). The corresponding contents figures for the synthetic mica platelets or the pigments based thereon can be seen from Table 6.

TABLE 6

| | Lead content [ppm] |
|---|---|
| Example 17 | <1 |
| Example 18 | <1 |
| Example 20 | <1 |
| Example 21 | <1 |

TABLE 5

Iron/titanium weight ratio of the pigments

| | Example 20 | Example 21 | Example 22 | Comparative example 1 | Comparative example 3 | Comparative example 4 | Comparative example 6 |
|---|---|---|---|---|---|---|---|
| $Fe_2O_3$ (% by weight) | 2.9 | 3.2 | 2.8 | 4.3 | 5.9 | 9.9 | 3.7 |
| $FeTiO_3$ (% by weight) | 5.4 | 6.1 | 5.3 | 8.1 | 11.3 | 18.8 | 7.1 |
| Fe (% by weight), calculated | 2.0 | 2.2 | 2.0 | 3.0 | 4.1 | 6.9 | 2.6 |
| $TiO_2$ (% by weight) | 23.9 | 33.4 | 9.7 | 30.2 | 24.7 | 30.4 | 28.0 |
| Fe/Ti weight ratio | 0.14 | 0.11 | 0.34 | 0.17 | 0.28 | 0.38 | 0.16 |
| Fe/Ti weight ratio (layer) | 4.37 | 4.21 | 4.60 | 6.16 | 9.54 | 16.28 | 5.01 |

IIIe Determination of the Chemicals Resistance

The chemicals resistance of the pigments from the inventive and comparative examples was determined on the basis of coatings applied to metal panels. 6 g of the pigment in question (in powder form) were incorporated by stirring into a mixture of 90 g of a conventional wet varnish based on hydroxy-functional acrylates (CSR varnish, colorless) and 10 g of butyl acetate 85. The viscosity was then adjusted using a mixture of butyl acetate 85 and xylene in a ratio of 1:1 to 17" in the DIN 4 mm cup. 100 g of this coating material in each case were applied coveringly to the metal panels in the same way as for IVa using an automatic sprayer. After coating had taken place, the metal panels were baked at 80° C. for 30 minutes.

24 hours later, one drop each of 10% strength by weight HCl and one drop of a 1 M aqueous sodium hydroxide solution were applied to each panel. After an exposure time of 0.5 h, 1 h, 2 h and 3 h, respectively, the HCl or NaOH drops were washed off with DI water and the panels were each inspected for damage to the coating film. Extreme damage, i.e. complete breakdown of the pigment, was given a score of 10, while no difference relative to the untreated panel was given a score of 0. The results of this inspection are reproduced in Table 7.

TABLE 7

Chemicals resistance

| Pigment from | Chemicals resistance | | |
|---|---|---|---|
| | Acid | Alkali | Sum |
| Example 20 | 0 | 0 | 0 |
| Example 21 | 0 | 2 | 2 |
| Example 22 | 0 | 1 | 1 |
| Comparative example 1 | 0 | 4 | 4 |
| Comparative example 2 | 5 | 10 | 15 |
| Comparative example 3 | 0 | 6 | 6 |
| Comparative example 4 | 3 | 4 | 7 |
| Comparative example 5 | 0 | 0 | 0 |
| Comparative example 6 | 0 | 3 | 3 |

The silver-colored pigments and also the conventional transparent silver-colored pearlescent pigment of the Phoenix series from Eckart (comparative example 5) are notable for their extremely high chemicals resistance.

IIIf Temperature Stability

For the purpose of testing the temperature stability, the pigments were stored at temperatures of 100° C. and 200° C. for 30 minutes in each case. On the basis of doctor-blade drawdowns of the respective pigment in a conventional nitrocellulose varnish (Dr Renger Erco Bronzemischlack 2615e; Morton, pigmentation level of 10% by weight, based on the total weight of the wet varnish) on black-white opacity charts (Byko-Chart 2853, Byk Gardner), any color changes that took place were assessed visually.

In this case it was found that on doctor-blade drawdowns of the silver-colored pigments there was no observable change in color after storage of the pigments either at 100° C. or at 200° C.

IIIg Lightness L*

The lightness L* of the nonmetallic platelet-shaped synthetic substrates was measured by diffuse colorimetry of the respective powder beds using the CR 310 colorimeter from Konica Minolta.

TABLE 8

| | Lightness L*, diffuse |
|---|---|
| Example 17 | 97.6 |
| Example 18 | 98.4 |
| Example 19 | 96.7 |

IIIh Diffuse Colorimetry

The lightness L*, a* and b* values and the chroma were determined by diffuse colorimetry of the respective powder beds, using a CM700d colorimeter from Konica Minolta.

TABLE 9

| Inventive/Comparative example | L* | a* | b* | C* | h° |
|---|---|---|---|---|---|
| Example 22 | 48.9 | −0.3 | 0.1 | 0.3 | 165.2 |
| Comparative example 7 | 49.5 | 12.4 | 14.3 | 19.0 | 49.2 |
| Comparative example 3 | 60.8 | −0.5 | 1.5 | 1.6 | 108.1 |
| Comparative example 4 | 50.6 | −1.6 | −4.1 | 4.4 | 249.4 |

Inventive example 22 is notable for low a* and b* values and hence also for low chroma values. The multilayer pearlescent pigment from comparative example 7 does have a silver interference color, but it is also clearly apparent from the chroma value that the pigment has a reddish brown absorption color. In the case of comparative examples 3 and 4 as well, in contrast to inventive example 22, at least one of the values, C*, a* or b*, is always increased, and so here as well it was possible to demonstrate the visually perceptible color tinge in a technical measurement.

IIIi Corrosion Resistance

The corrosion resistance of the silver-colored pigments of the cosmetic formulation was determined by determination of the gassing behavior in an aqueous carbomer gel system. For this purpose, first of all, a carbomer gel consisting of 0.7% by weight of Aristoflex AVC gel former from Clariant and 99.3% by weight of DI water was prepared with stirring. Then a suspension of 23% by weight of silver-colored pigment and 77% by weight of DI water was added with stirring to the carbomer gel. This mixture was admixed with 1% by weight, based on its total weight, of the preservative Uniphen P-23, in order to prevent microbial colonization and possibly falsification of the measurement result as a result of gas secretion by the microbes. Subsequently, 300 g of the resulting mixture were introduced into a gas wash bottle, closed off with a double-chamber gas bubble counter, and then heated to 40° C. in a water bath. The evolution of gas was determined over a period of 30 days. After these 30 days, there was no gas evolution observed with the silver-colored pigments. The test is passed if the gas evolution after 30 days is <10 ml. Ideally no gas evolution is observed.

IV Characterization of the Optical Effect of the Silver-Colored Pigments

Characterization took place as described below on the basis of the silver-colored pigment.

IVa Determination of the Light/Dark Flop (Flop Index)

The flop index of the pigments from the inventive and comparative examples was determined on the basis of coatings applied to metal panels. 6 g of the respective pigment (in powder form) were incorporated with stirring into a mixture of 90 g of a conventional wet varnish based on hydroxy-functional acrylates (CSR varnish, colorless) and 10 g of butyl acetate 85. The viscosity was subsequently adjusted using 25 g of a mixture of butyl acetate 85 and xylene in a ratio of 1:1 to 17" in the DIN 4 mm cup.

100 g of this coating material in each case were applied to metal panels using an automatic sprayer and the LP-90 spray gun with 1.3.5 needle setting (both from Languth) with a pressure of 4 bar (6 passes). After a flash-off time of 15 minutes, a further clear coat layer (70 g of KL Autoclear Plus and 42 g of Härter P25 curing agent, each from Sikkens) was applied with a pressure of 4 bar in 3 passes (needle setting: 2.0.3). After coating had taken place, the metal panels were baked at 80° C. for 30 minutes.

The flop index is defined in accordance with Alman as follows (S. Schellenberger, M. Entenmann, A. Hennemann, P. Thometzek, Farbe and Lack, 04/2007, p. 130):

$$\text{Flop index} = 2.69 \cdot (L_{E1} - L_{E3})^{1.11} / L_{E2}^{0.86}$$

where $L_{E1}$ is the lightness of the near-specular measuring angle (E1=15° relative to the specular angle), $L_{E2}$ is the lightness of the measuring angle between near-specular and far-specular angle (E2=45° relative to the specular angle), and $L_{E3}$ is the lightness of the far-specular measuring angle (E3=110° relative to the specular angle).

The larger the numerical value of the flop index, the more greatly the light/dark flop is expressed.

For the determination of the flop index, the lightness L* was measured by multiangle colorimetry using the Bykmac instrument from Byk Gardner. The corresponding values are listed in Table 10.

Examples 20 and 22 in fact have a higher flop index than a comparable metallic pigment (comparative example 2). Example 21 possesses a lower flop index, this being attributable to the smaller particle size and the greater degree of scattering associated therewith. As compared with a metallic effect pigment having a similar particle size distribution, the flop index of the silver-colored pigment, here as well, is slightly above that of the comparable metallic effect pigment. Comparative example 3 possesses a comparably high flop index. This comparably high flop index is favored by the greater coloration of the pigment. In visual terms, however, the pigment is not color-neutral (chroma) and therefore almost wholly unsuitable as an imitation or substitute for an aluminum effect pigment.

IVb Effect Measurements

Effect measurements for determining the glitter effect of the pigments were carried out on the basis of the spray applications from IVa, using a BYK-mac (Byk-Gardner).

To simulate effect changes upon direct illumination, the glitter effect is investigated with the BYK-mac, using a high-resolution CCD camera. The glitter effect, caused by the reflecting ability of the individual effect pigments, is perceived only upon direct solar irradiation, and changes depending on the angle of illumination. For this reason, the sample in the Byk-mac is illuminated with very bright LEDs at three different angles) (15°/45°/75°. Using the CCD camera, an image is recorded in each case perpendicularly to the surface. The images are analyzed using image processing algorithms, with the histogram of the lightness stages being used as a basis for calculating the glitter parameters. In order to ensure improved differentiation, the glitter effect was described using a two-dimensional system, the glitter area S_a and the glitter intensity S_i. Alternatively, this data was summarized in a one-dimensional value, the glitter degree S_G. The corresponding measurement values are collated in Table 10.

Critical to the visual impression is the one-dimensional glitter degree S_G. The higher the numerical value of S_G, the higher the glitter effect perceptible to the eye. In a two-dimensional representation, the glitter degree S_G can be broken down into the components of glitter intensity S_i and glitter area S_a. Since both components have a critical influence on the glitter degree S_G, it may happen that an effect pigment has virtually the same glitter degree S_G in the 15°, 45° and 75° measurement geometries, despite the fact that the numerical values of S_a and S_G in the measurement geometries under consideration are significantly increased or lowered.

In terms of their glitter intensity S_i, the silver-colored pigments are superior to pearlescent pigments based on natural mica platelets. In a comparison of glitter area S_a, glitter intensity S_i, glitter degree S_G, and flop index, it is necessary to take into account the average particle size $D_{50}$. In other words, only pigments with the same or similar average particle size are comparable with one another. A lower average particle size $D_{50}$, such as in example 21, is manifested in lower figures for glitter area S_a, glitter intensity S_i, glitter degree S_G, and flop index.

The measurement values for lightness, chroma, flop index, S_g, S_a, and S_i that are shown in Table 10 were determined on the basis of the spray applications in IIIa.

TABLE 10

Lightness L*, chroma, flop index, glitter area S_a, glitter intensity S_i, glitter degree S_G of the pigments

| | Measurement geometry | Lightness L* | Chroma | Flop index | S_G [15°] | S_i [15°] | S_a [15°] |
|---|---|---|---|---|---|---|---|
| Example 20 | 15° | 132.8 | 0.5 | 21.4 | 6.7 | 14.7 | 31.1 |
| | 25° | 92.0 | 0.8 | | | | |
| | 45° | 45.3 | 1.3 | | | | |
| | 75° | 26.1 | 1.9 | | | | |
| | 110° | 20.2 | 1.6 | | | | |
| Example 21 | 15° | 120.3 | 0.67 | 15.8 | 4.4 | 9.1 | 24.1 |
| | 25° | 92.7 | 0.51 | | | | |
| | 45° | 53.4 | 0.91 | | | | |
| | 75° | 30.8 | 1.21 | | | | |
| | 110° | 22.9 | 0.93 | | | | |
| Example 22 | 15° | 116.0 | 0.4 | 20.0 | 12.3 | 33.0 | 21.2 |
| | 25° | 78.6 | 0.9 | | | | |
| | 45° | 37.5 | 1.7 | | | | |
| | 75° | 27.1 | 2.1 | | | | |
| | 110° | 24.4 | 1.6 | | | | |
| Comparative example 1 | 15° | 126.0 | 1.0 | 16.8 | 3.7 | 7.7 | 24.1 |
| | 25° | 95.8 | 0.5 | | | | |
| | 45° | 53.3 | 0.8 | | | | |
| | 75° | 30.7 | 1.0 | | | | |
| | 110° | 23.2 | 0.8 | | | | |
| Comparative example 2 | 15° | 149.8 | 0.4 | 19.1 | 5.2 | 11.0 | 26.6 |
| | 25° | 109.7 | 0.36 | | | | |
| | 45° | 56.9 | 0.50 | | | | |
| | 75° | 34.0 | 0.73 | | | | |
| | 110° | 28.5 | 1.22 | | | | |
| Comparative example 3 | 15° | 120.3 | 1.76 | 20.2 | 4.7 | 10.0 | 24.7 |
| | 25° | 87.0 | 2.10 | | | | |
| | 45° | 43.4 | 2.36 | | | | |
| | 75° | 23.3 | 2.68 | | | | |
| | 110° | 16.9 | 2.41 | | | | |
| Comparative example 4 | 15° | 83.8 | 1.41 | 10.3 | 0.8 | 2.7 | 7.9 |
| | 25° | 72.5 | 0.82 | | | | |
| | 45° | 50.4 | 1.69 | | | | |
| | 75° | 30.7 | 2.57 | | | | |
| | 110° | 20.3 | 2.15 | | | | |

TABLE 10-continued

Lightness L*, chroma, flop index, glitter area S_a, glitter intensity S_i, glitter degree S_G of the pigments

|  | Measurement geometry | Lightness L* | Chroma | Flop index | S_G [15°] | S_i [15°] | S_a [15°] |
|---|---|---|---|---|---|---|---|
| Comparative example 5 | 15° | 140.4 | 1.5 | 9.8 | 3.8 | 8.1 | 20.9 |
|  | 25° | 109.6 | 1.3 |  |  |  |  |
|  | 45° | 72.3 | 2.1 |  |  |  |  |
|  | 75° | 59.5 | 3.1 |  |  |  |  |
|  | 110° | 60.1 | 2.5 |  |  |  |  |
| Comparative example 6 | 15° | 125.8 | 0.5 | 16.2 | 3.1 | 6.6 | 18.3 |
|  | 25° | 96.5 | 0.9 |  |  |  |  |
|  | 45° | 54.2 | 1.8 |  |  |  |  |
|  | 75° | 31.8 | 2.6 |  |  |  |  |
|  | 110° | 24.9 | 2.1 |  |  |  |  |
| Comparative example 7 | 15° | 97.1 | 18.0 | 11.6 | 6.6 | 13.7 | 32.5 |
|  | 25° | 69.8 | 28.5 |  |  |  |  |
|  | 45° | 43.3 | 49.6 |  |  |  |  |
|  | 75° | 36.7 | 59.5 |  |  |  |  |
|  | 110° | 34.5 | 62.1 |  |  |  |  |
| Comparative example 8 | 15° | 119.8 | 1.2 | 1.9 | 0.9 | 2.1 | 7.8 |
|  | 25° | 105.8 | 0.9 |  |  |  |  |
|  | 45° | 84.7 | 1.2 |  |  |  |  |
|  | 75° | 73.7 | 0.2 |  |  |  |  |
|  | 110° | 72.0 | 0.7 |  |  |  |  |

TABLE 11

|  | Flop index/D50 | Flop intensity $F_i$ = (Flop index · S_i)/D50 |
|---|---|---|
| Example 20 | 0.9 | 13.2 |
| Example 21 | 1.2 | 10.8 |
| Example 22 | 0.6 | 19.2 |
| Comparative example 1 | 0.7 | 5.3 |
| Comparative example 2 | 1.0 | 10.6 |
| Comparative example 3 | 1.0 | 9.5 |
| Comparative example 4 | 1.6 | 4.3 |
| Comparative example 5 | 0.5 | 3.9 |
| Comparative example 6 | 0.7 | 4.5 |
| Comparative example 7 | 0.4 | 5.4 |
| Comparative example 8 | 0.6 | 1.3 |

With the exception of comparative example 2, the values for the flop intensity of all of the comparative examples are <10 and therefore have no sufficient metallic character in visual terms. In the case of comparative example 2, the pigment in question is a metallic effect pigment. The silver-colored pigments from examples 20 to 22, for use in the cosmetic formulation of the invention, possess flop intensities of >10 and therefore exhibit outstanding metallic character.

IVc Gloss Measurements

The gloss is a measure of the directed reflection and can be characterized precisely using a Micro-Tri-Gloss instrument. More strongly scattering samples ought to exhibit a low gloss, owing to increased edge scattering and also to pigment unevennesses.

The applied coatings on black-white opacity charts were subjected to measurement using a Micro-Tri-Gloss gloss meter, from Byk Gardner, with a measurement angle of 60° relative to the vertical. The respective pigments were incorporated with stirring into a conventional nitrocellulose varnish (Dr Renger Erco Bronzemischlack 2615e; from Morton, level of pigmentation 10% by weight, based on the total weight of the nitrocellulose varnish). The completed varnish was applied using a doctor-blade drawdown apparatus with a wet-film thickness of 76 μm to black-white opacity charts (Byko-Chart 2853, Byk-Gardner).

The gloss values set out in Table 12 below represent average values from five individual measurements in each case.

The silver-colored pigments have a significantly stronger gloss than the comparative examples. An exception is comparative example 5. Owing to the high transparency of this pigment, the white substrate of the opacity chart is included in the measurement.

IVd Opacity

The opacity of the pigments from the inventive and comparative examples was determined on the basis of the coatings applied to black-white opacity charts from IVc. The lightness values L* were measured with a measurement geometry of 110°, relative to the angle of emergence of the light irradiated at 45°, on the basis of these coatings applied to the black background and to the white background of the black-white opacity chart, using the Byk-mac instrument from Byk Gardner. By formation of the opacity quotient Dq it is possible to determine numerical dimensions for the opacity of the pigments that are independent of the substrate. For this purpose, the quotient of the lightness values on the black background to the lightness values on the white background of the black-white opacity chart is calculated:

$$Dq = \frac{L*_{110,black}}{L*_{110,white}}$$

Where the coating systems used are identical, the opacity quotient permits a comparison of the opacity of different effect pigments with one another.

The silver-colored pearlescent pigments from example 20 achieve an opacity comparable with that of aluminum effect pigments of the same average particle size (comparative example 2).

Comparative examples 3 and 4 do possess a very good opacity, but because of the very low gloss and also the high chroma values, they are by no means metallic and are extremely unattractive in visual terms.

TABLE 12

Opacity quotient and gloss

|  | Opacity quotient 110° Byk-mac | Gloss [60°] |
|---|---|---|
| Example 20 | 0.630 | 32.1 |
| Example 21 | 0.760 | 19.6 |
| Example 22 | 0.527 | 23.0 |
| Comparative example 1 | 0.524 | 25.3 |
| Comparative example 2 | 1.001 | 19.8 |
| Comparative example 3 | 0.654 | 17.5 |
| Comparative example 4 | 0.938 | 17.4 |
| Comparative example 5 | 0.393 | 38.5 |

The invention claimed is:

1. A cosmetic formulation comprising a cosmetically acceptable medium and at least one silver-colored pigment, the silver-colored pigment having a metallic character or effect and comprising a nonmetallic platelet-shaped substrate, at least one titanium oxide layer, and at least one ilmenite-containing coating,
   wherein the amount of iron compounds, calculated as elemental iron, in the pigment is less than 5.0% by weight, based on the total weight of the silver-colored pigment,
   wherein the at least one ilmenite-containing coating has a concentration gradient which decreases in the substrate direction, and
   wherein the silver-colored pigment has a flop intensity $F_i$, defined as the product of flop index and glitter intensity S—i as a function of the average particle size $D_{50}$, in accordance with formula (II)

$$\text{Flop intensity } (F_i) = \frac{\text{Flop index} \cdot S\_i}{D_{50}}, \quad (II)$$

of at least 10.

2. The cosmetic formulation according to claim 1, wherein the silver-colored pigment has an iron(III) oxide content of less than 0.5% by weight, based on the total weight of the pigment.

3. The cosmetic formulation according to claim 1, wherein the chroma of the silver-colored pigment with a measurement geometry of 110°, relative to the angle of emergence of the light irradiated at 45°, is $C^*_{110} < 2.4$.

4. The cosmetic formulation according to claim 1, wherein the-ilmenite-containing coating layer of the silver-colored pigment has an average layer thickness in a range from 1 nm to 20 nm.

5. The cosmetic formulation according to claim 1, wherein the silver-colored pigment has an iron/titanium weight ratio as a function of the coating, in accordance with formula (I)

$$\frac{\text{Iron content (\% by weight)}}{\text{Titanium content (\% by weight)}} \quad (I)$$

Fraction of the coating (% by weight), in a range from 1 to 8, where "iron content" stands for the amount of iron compounds, calculated as elemental iron, and "titanium content" stands for the amount of titanium compounds, calculated as elemental titanium, in each case in the pigment and based on the total weight of the silver-colored pigment, and where the "fraction of the coating (% by weight)" stands for the weight fraction, based on the total weight of the pigment, of the coating applied to the substrate.

6. The cosmetic formulation according to claim 1, wherein the silver-colored pigment comprises the following construction:

(a) nonmetallic platelet-shaped synthetic substrate,
(b) titanium oxide layer, and
(c) ilmenite layer.

7. The cosmetic formulation according to claim 1, wherein the nonmetallic platelet-shaped substrate of the silver-colored pigment is selected from the group consisting of synthetic mica platelets, glass platelets, $SiO_2$ platelets, $Al_2O_3$ platelets, synthetic boehmite platelets, polymer platelets, synthetic platelet-shaped substrates which comprise an inorganic-organic hybrid layer, and mixtures thereof.

* * * * *

UNITED STATES PATENT AND TRADEMARK OFFICE
CERTIFICATE OF CORRECTION

PATENT NO. : 9,084,732 B2
APPLICATION NO. : 13/428567
DATED : July 21, 2015
INVENTOR(S) : Michael Grüner et al.

It is certified that error appears in the above-identified patent and that said Letters Patent is hereby corrected as shown below:

Claims

Column 43, Line 1, Claim 1, delete "S-i" and insert -- $S\_i$ --

Column 43, Line 14, Claim 3, delete "C*110<2.4." and insert -- $C*110 \leq 2.4$. --

Signed and Sealed this
Sixteenth Day of February, 2016

Michelle K. Lee
*Director of the United States Patent and Trademark Office*